(12) United States Patent
Ryttsén et al.

(10) Patent No.: US 7,456,012 B2
(45) Date of Patent: *Nov. 25, 2008

(54) METHOD AND APPARATUS FOR SPATIALLY CONFINED ELECTROPORATION

(75) Inventors: Frida Ryttsén, Göteborg (SE); Owe Orwar, Hovås (SE); Mikael Levin, Hisings Backa (SE); Eskil Sahlin, Göteborg (SE); Joakim Wigström, Västra Frölunda (SE)

(73) Assignee: Cellectricon AB, Gothenburg (SE)

( * ) Notice: Subject to any disclaimer, the term of this patent is extended or adjusted under 35 U.S.C. 154(b) by 328 days.

This patent is subject to a terminal disclaimer.

(21) Appl. No.: 10/726,381

(22) Filed: Dec. 2, 2003

(65) Prior Publication Data

US 2005/0048651 A1    Mar. 3, 2005

Related U.S. Application Data

(63) Continuation-in-part of application No. 10/345,107, filed on Jan. 15, 2003, and a continuation-in-part of application No. 10/325,691, filed on Dec. 19, 2002, now Pat. No. 7,109,034, which is a continuation of application No. 09/557,979, filed on Apr. 25, 2000, now Pat. No. 6,521,430, which is a continuation of application No. PCT/SE98/02012, filed on Nov. 6, 1998.

(60) Provisional application No. 60/356,377, filed on Feb. 12, 2002.

(51) Int. Cl.
*C12M 1/42* (2006.01)

(52) U.S. Cl. ............... 435/285.2; 435/305.2; 435/461

(58) Field of Classification Search .............. None
See application file for complete search history.

(56) References Cited

U.S. PATENT DOCUMENTS

| | | | |
|---|---|---|---|
| 3,867,201 A * | 2/1975 | Holmes | 429/118 |
| 6,208,893 B1 | 3/2001 | Hofmann | |
| 6,241,666 B1 | 6/2001 | Pomeranz et al. | |
| 6,278,895 B1 | 8/2001 | Bernard | |
| 6,326,177 B1 | 12/2001 | Schoenbach et al. | |
| 6,455,303 B1 | 9/2002 | Orwar et al. | |
| 6,521,430 B1 | 2/2003 | Orwar et al. | |
| 7,018,819 B2 | 3/2006 | Orwar et al. | |
| 7,109,034 B2 * | 9/2006 | Orwar et al. | 435/461 |
| 2002/0076689 A1 | 6/2002 | Farb et al. | |
| 2003/0014081 A1 | 1/2003 | Bernabei | |
| 2004/0029101 A1 | 2/2004 | Orwar et al. | |
| 2004/0110307 A1 | 6/2004 | Karlsson et al. | |
| 2004/0112529 A1 | 6/2004 | Karlsson et al. | |
| 2004/0181343 A1 | 9/2004 | Wigstrom et al. | |
| 2004/0182707 A1 | 9/2004 | Jardemark et al. | |
| 2005/0026283 A1 | 2/2005 | Ormar et al. | |
| 2006/0223164 A1 | 10/2006 | Orwar et al. | |

FOREIGN PATENT DOCUMENTS

| | | |
|---|---|---|
| EP | 0 986 758 B1 | 12/1998 |
| WO | WO 95/23211 A1 | 8/1995 |
| WO | WO-99/24110 A1 | 5/1999 |
| WO | WO-01/09297 A1 | 2/2001 |
| WO | WO 01/43817 A1 | 6/2001 |
| WO | WO-02/33066 A1 | 4/2002 |
| WO | WO 03/013647 A2 | 2/2003 |
| WO | WO-03/046170 A1 | 6/2003 |
| WO | WO-03/046171 A1 | 6/2003 |
| WO | WO-03/068906 A1 | 8/2003 |
| WO | WO 2004/039489 A2 | 5/2004 |

\* cited by examiner

*Primary Examiner*—James S Ketter
(74) *Attorney, Agent, or Firm*—Edwards Angell Palmer & Dodge LLP; David G. Conlin; Jeffrey L. Kopacz

(57) ABSTRACT

The invention provides hollow-tip-electrodes for spatially localized delivery of substances to one or more biological targets present in a population comprising target and non-target molecules, macromolecules, and/or cells. The invention also provides electrode plates for receiving one or more of such tips, tip-electrode plates comprising electrode plates comprising one or more electrode tips, and systems comprising tip-electrodes and containers for containing one or more biological targets, e.g., such as molecules, macromolecules, and/or cells. The invention further provides methods for using such systems and components thereof. In one preferred aspect, the systems are used for spatially confined electroporation of cells and cell structures. The invention facilitates high throughput screening of agents (e.g., such as drugs) that act on intracellular targets.

139 Claims, 14 Drawing Sheets

Figures 13A-G

FIGURE 14
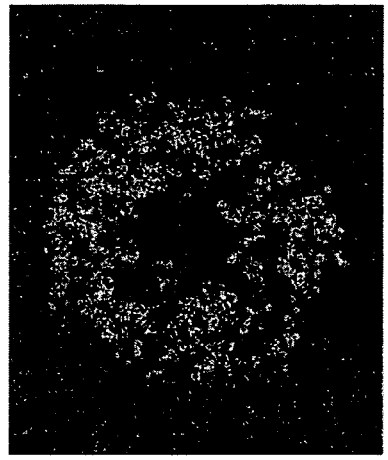
Fig. B
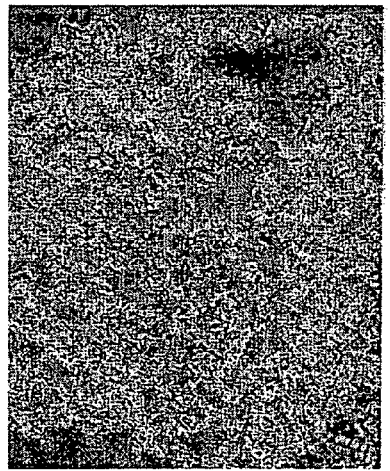
Fig. A
Fig. E
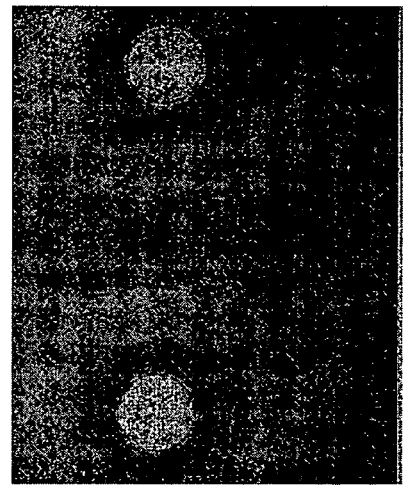
Fig. D
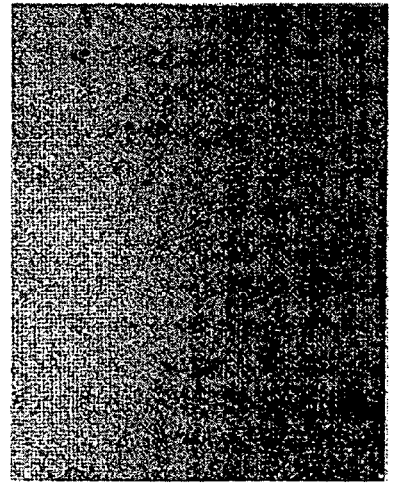
Fig. C

US 7,456,012 B2

METHOD AND APPARATUS FOR SPATIALLY CONFINED ELECTROPORATION

RELATED APPLICATIONS

This application is a continuation-in-part of U.S. patent application Ser. No. 10/325,691, filed Dec. 19, 2002, now U.S. Pat. No. 7,109,034 which is a continuation of U.S. patent application Ser. No. 09/557,979, now U.S. Pat. No. 6,521,430, filed Apr. 25, 2000, which is a continuation application of International Application No. PCT/SE98/02012, filed Nov. 6, 1998, which claims priority to Swedish Application No. 9704076-0, filed Nov. 6, 1997 and is also a continuation in part of U.S. patent application Ser. No. 10/345,107, filed Jan. 15, 2003, which claims priority to U.S. Provisional Application No. 60/356,377, filed Feb. 12, 2002. The entireties of these applications are incorporated by reference herein.

FIELD OF THE INVENTION

The present invention relates to a method for electroporation and delivery of one or more agents to spatially confined targets, such as populations of cells, single cells, intracellular organelles, and biomolecules.

BACKGROUND OF THE INVENTION

During the last two decades there has been a tremendous growth in experimental methods that allow for biochemical and biophysical investigations of single cells. Such methods include patch clamp recordings which can be used for measurement of transmembrane currents through a single ion channel (Hamill, et al., *Pfleugers Arch.* 391: 85-100, 1981); laser confocal microscopy imaging techniques that can be used to localize bioactive components in single cells and single organelles (Maiti, et al., *Science* 275: 530-532, 1997); use of near field optical probes for pH measurements in the cell interior; and use of ultramicroelectrodes for measurement of release of single catechol- and indol-amine-containing vesicles (Chow, et al., *Proc. Natl. Acad. Sci. USA.* 88: 10754-10758, 1991).

Highly specific enzymes, substrates and protein probes are available that makes it possible to detect particular components in cells. (Tsien, *Annu. Rev. Biochem.* (1998), 67: 509-544). The major challenge, so far, in applying such probes, drugs, and other effectors of intracellular chemistry is in introducing them into the cellular interior. Many of these agents (e.g., nanoparticles, dyes, drugs, DNAs, RNAs, proteins, peptides, and amino acids) are polar, and polar solutes are cell-impermeable and unable to pass biological membranes. Thus, the cell plasma membrane barrier acts as a physical boundary to the external solution and prevents the entrance of exogenous compounds and particles. At present, it is extremely difficult, for example, to label a cell in a cell culture with a dye, or transfect it with a gene without labelling or transfecting its adjacent neighbor. It is even more difficult to introduce polar molecules into organelles because of their size which many times is smaller than the resolution limit of a light microscope, or at least less than a few micrometers in diameter.

Microinjection techniques for single cells and single nuclei have also been described (see, e.g., Capecchi, *Cell* 22: 479-488, 1980, but these get increasingly difficult to implement as the size of the cell or organelle decreases. For cells and organelles measuring only a few micrometers in diameter or less, microinjection techniques become virtually impossible to use.

Cell membranes can be permeabilized by pulsed electric fields (see e.g. Zimmermann, *Biochim. Biophys Acta*, (1982) 694: 227-277). This technique is called electroporation. The event that leads to breakdown of the plasma membranes is the induction of a transmembrane potential over a critical value, by the applied electric field. The transmembrane potential $\Delta V$, for a spherical cell of radius rc in a homogeneous electric field, E, is generally calculated from:

$$\Delta V = 1.5 r_c E \cos \alpha (1 - e^{-t/\tau}) \quad (1)$$

where 1.5 is a geometric factor, and $\alpha$ is the angle between the location at the membrane and the direction of the field. t is the pulse duration and $\tau$ is the time it takes for the membrane to achieve the induced transmembrane potential, and is described by:

$$\tau = r_c C_m (\rho_i + 0.5 \rho_e) \quad (2)$$

where $C_m$ is the specific membrane capacitance per unit area, and $\rho i$ and $\rho e$ are the resistivities of the intracellular and extracellular solutions, respectively.

The electroporation technique is widely used on large populations of cells (in the order of $10^6$ cells). Typically, cells are placed between large, plate-electrodes which generate homogeneous electric fields. Instrumentation that can be used for electroporation of a small number of cells in suspension (Kinosita and Tsong, *Biochim. Biophys. Acta* 554: 479-497, 1979); Chang, *J. Biophys.* 56: 641-652, 1989; Marszalek, et al., *Biophys. J.* 73: 1160-1168, 1997) and for a small number of adherent cells grown on a substratum (Zheng, *Biochim. Biophys. Acta* 1088: 104-110, 1991); Teruel and Meyer, *Biophys. J.*, 73: 1785-1796, 1997) have also been described. The design of the electroporation device constructed by Marszalek, et al., 1997, supra, is based on 6 mm long 80 μm diameter platinum wires that are glued in a parallel arrangement at a fixed distance of 100 μm to a single glass micropipette. The design by Kinosita and Tsong, 1979, supra, uses fixed brass electrodes spaced with a gap distance of 2 mm. The microporator design of Teruel and Meyer, 1997, supra, relies on two platinum electrodes that are spaced with a gap distance of about 5 mm, and the electroporation chamber design by Chang uses approximately 1 mm-long platinum wires spaced at a distance of 0.4 mm.

These electroporation devices, which are optimized for usage in vitro, create electric fields that are several orders of magnitude larger than the size of a single cell which typically is 10 μm in diameter, and thus can not be used for exclusive electroporation of a single cell or a single organelle or for electroporation inside a single cell. The techniques do not offer a sufficient positional and individual control of the electrodes to select a single cell, or a small population of cells. Furthermore, these techniques are not optimized for electroporation in vivo or for electroporation of remote cells and tissue.

Electroporation devices for clinical and in vivo applications have also been designed. Examples include devices for electroporation-mediated delivery of drugs and genes to tumors (WO 96/39226) and to blood cells (U.S. Pat. No. 5,501,662) and to remote cells and tissue (U.S. Pat. No. 5,389,069). Likewise, these cannot be used to create a highly localized electric field for spatially confined electroporation.

SUMMARY

The invention provides methods and devices for providing spatially localized electric fields to a variety of targets, including, but not limited to cells and cell structures. In particular, in one aspect, the invention provides methods for screening for agents which modulate the activities of intracellular molecules, such as intracellular receptors, the cytoplasmic domains of cell membrane molecules, organellar receptors, enzymes, and molecules involved in signaling and metabolic pathways. The devices according to the invention enable high throughput screening for such agents.

In one aspect, the invention provides a tip-electrode comprising: a housing defining a lumen for receiving an electrically conductive medium; and an electrically conducting surface for coupling to a voltage or current generator. Preferably, the housing comprises a target-facing end comprising an opening in communication with the lumen for delivering an agent through the opening to a target. The lumen may additionally, or alternatively, comprise an electrically conductive medium (e.g., a liquid, a gel, and the like).

Exemplary agents include, but are not limited to, genes; gene analogs; RNA; RNA analogs; siRNA; antisense oligonucleotides; ribozymes; DNA; DNA analogs; aptamers; colloidal particles; nanoparticles; receptors; receptor ligands; receptor antagonists; receptor agonists; receptor blockers; enzymes; enzyme substrates; enzyme inhibitors; enzyme modulators, proteins; protein analogs; polypeptides; polypeptide analogs; amino acids; amino acid analogs; peptides; peptide analogs; metabolites; metabolite analogs' oligonucleotides; oligonucleotide analogs; antigens; antigen analogs; haptens; hapten analogs; antibodies; antibody analogs; organelles; organelle analogs; cell nuclei; cell fractions; bacteria; viruses; viral particles; gametes; inorganic ions; organic ions; metal; agents that affects cellular chemistry; agents that affect the cytoskeleton, agents that affect polymers and combinations thereof.

In one aspect, the housing comprises a tapered end to facilitate its insertion into a biological membrane.

In another aspect, the lumen of the housing comprises an element comprising an electrically conducting surface. For example, the element may be in the form of electrically conducting surface is a structure penetrating the walls of the housing on one or both sides of the housing. For example, the electrically conducting surface may be a wire connected on the outside of the housing to a ring plate.

The tip electrode may be used for agent delivery and in one aspect, the electrically conductive medium comprises an agent for delivery to a target.

The housing may be constructed from a variety of materials, including, but not limited to: glass, fused silica, plastic, ceramic, an elastomeric material, a polymer, metal, a non-conducting material coated at least partially with a conducting material, and a conducting material coated at least partially with a non-conducting material.

In one aspect, the housing further comprises a receiving end distal to the target-facing end and comprises an opening for receiving an electrically conductive medium.

In another aspect, the tip electrode further comprises a conducting surface which functions as a counter electrode.

In a further aspect, the housing comprises a uniform inner diameter and uniform or varying outer diameter. In one aspect, the length of the tip electrode is less than about 10 cm. In another aspect, the length of the tip electrode is less than about 500 μm. In still another aspect, the length of the tip electrode is less than about 50 μm. In a further aspect, the length of the tip electrode is less than about 1 μm.

In one aspect, the diameter of the opening at a target-facing end of the tip electrode is less than or equal to about 5000 μm. Preferably, the diameter of the opening at the target-facing end is less than about 100 μm. More preferably, the diameter of the opening at the target-facing end is less than about 50 μm, less than about 10 μm, less than about 1 μm, less than about 100 nm, or than about 50 nm.

The invention further provides an electrode plate comprising at least one mounting point for receiving a tip electrode. In one aspect, the at least one mounting point comprises a flexible attachment point for receiving the tip electrode, permitting vertical movement of a tip-electrode from the mounting point. Preferably, the electrode plate, comprises a plurality of mounting points. For example, the plate may comprise a row of mounting points for forming a linear array of tip-electrodes. Alternatively, the plate may comprise a plurality of rows of mounting points for forming a two-dimensional array of tip-electrodes. In one aspect, the center-to-center distance of each mounting point corresponds to the center-to-center distance of wells in an industry standard microtiter plate.

Preferably, the electrode plate comprises at least one interface point for a voltage or current generator. Also, preferably, the electrode plate comprises at least one interface point for interfacing with a fluid delivery device.

In one aspect, the electrode plate comprises at least two layers including a conducting layer and an insulating layer. Further, a layer of the electrode plate may function as a counter electrode.

Preferably, an electrode plate comprising at least one mounting point further comprises an aperture for receiving the tip-electrode and in one aspect, the invention further provides an electrode plate wherein at least one tip-electrode is mounted to the electrode plate at the mounting point. Preferably, a plurality of tip electrodes are mounted to the electrode plate.

In one aspect, the electrode plate comprises at least one microfluidic channel for delivering fluids to at least on tip electrode mounted to the plate.

The invention further provides a tip-electrode plate comprising a substantially planar plate on which at least one non-planar element is fabricated thereon wherein an end of the non-planar element distal from the plate comprises an opening for exposing a target to an electric field and wherein inner walls of the non-planar element define a lumen for containing an electrically conductive medium. In one aspect, the inner walls comprise an electrically conductive surface. For example, the electrically conductive surface may comprise a conductive coating that at least partially coats the inner walls of the lumen. Preferably, the end of the at least one non-planar element is tapered.

In one aspect, the tip electrode plate comprises a first layer comprising a plurality of reservoirs and a substantially planar second layer comprising a plurality of nonplanar elements elevated above the plate. Preferably, each nonplanar element comprises a target-facing opening for exposing a target to an electric field. The opening is centered above each reservoir in the first layer, and inner walls of the nonplanar element define a lumen communicating both with the reservoir and the opening.

The plate may further comprise a counter electrode layer. The reservoirs may additionally comprise an electrically conductive medium. Preferably, the electrically conductive medium comprises an agent.

In one aspect, the counter electrode layer contacts the electrically conductive medium.

The invention further provides a kit comprising any of the tip electrodes described above and a container for containing a target. Suitable containers include, but are not limited to: a microtiter dish, a multi-well cell culture container, a petrie dish, polymeric substrate, a glass substrate, a microfluidic chip, and a membrane. In one aspect, the kit further provides an electrode plate for receiving the tip electrode. In another aspect, the electrode plate and/or the container comprises at least one microfluidic channel. In another aspect, the kit further comprises at least one counter electrode. In still another aspect, the kit comprises an electrically conductive medium for filling at least one tip-electrode. In a further aspect, the kit comprises at least one agent and/or a target (e.g., cells, cell structures, and the like).

The invention also provides a system comprising at least one tip electrode, such as any of the tip electrodes described above. In one aspect, the system comprises an electrically conducting surface in contact with an electrode plate as described above and a tip electrode. Preferably, the housing comprises a target-facing end comprising an opening in communication with the lumen for delivering an agent through the opening to a target. Also, preferably, the electrode plate is connectable to a pulse generator for delivering a voltage or current pulse to the electrically conducting surface. Further, preferably, the system comprises a container for containing a target.

In another aspect, the system further comprises a mechanism for positioning the at least one tip-electrode in proximity to a target and a pulse generator in communication with the electrode plate for delivering voltage or current pulses through the at least one tip electrode. Preferably, the system further comprises at least one counter electrode.

In a further aspect, the system additionally comprises a delivery mechanism for delivering a fluid and/or an agent to at least one tip electrode. The delivery mechanism may comprise one or more of: a pumping mechanism, a mechanism for electroosmosis, or a mechanism for electrophoresis of an agent through the lumen of the tip electrode.

In one aspect, the system comprises a plurality of tip electrodes, each in electrical contact with the electrode plate. The tip electrodes may be detachable from the electrode plate or an integral part thereof. Electrical pulses are transmitted through each tip electrode and preferably are independently controlled through a system processor. The plurality of tip electrodes may comprise an arrayed arrangement (e.g., in rows). The electrode plate and/or container may further comprise one or more microfluidic channels.

In one preferred aspect, the system further comprises a detector, for detecting alteration of electrical properties or optical properties of a target proximity to a tip electrode and/or delivery of a fluid and/or agent to the target.

In another aspect, the electrode plate comprises a first layer comprising a plurality of reservoirs and a substantially planar second layer comprising a plurality of nonplanar elements elevated above the plate forming the tip electrodes. The target-facing opening of the tip electrode is centered above each reservoir in the first layer, and the lumen of the tip electrode communicates with the reservoir. In one aspect, the lumen of the at least one tip electrode comprises an electrically conductive medium. Preferably, the housing of the at least one tip electrode comprises a tapered end. Also, preferably, the electrically conducting surface of the at least one tip electrode comprises a coating at least partially coating walls of the housing defining the lumen. However, alternatively, or additionally, the electrically conducting surface comprises an element comprising an electrically conducting surface inserted into the lumen of the housing. For example, the element may be a cylinder, rod or wire. In one aspect, the electrically conducting surface is a structure penetrating the walls of the housing on one or both sides of the housing. In another aspect, the electrically conducting surface is a wire connected on the outside of the housing to a ring plate. The electrically conductive medium may also be a liquid or a gel and in one aspect, the electrically conductive medium comprises an agent for delivery to a target.

In one preferred aspect, the system further comprises a processor for controlling one or more parameters selected from the group consisting of: delivery of fluid to the at least one tip electrode, delivery of at least one agent to at least one tip electrode, filling of the tip electrode with an electrically conductive medium, voltage or current pulse parameters (e.g., pulse duration, waveform, and pulse amplitude), scanning of the electrode plate comprising the at least one tip electrode relative to a target, scanning of a target relative to a tip electrode, vertical movement of a tip electrode, electrophoresis through a tip electrode, electroosmosis through a tip electrode, pumping of fluid through a tip electrode, and a function of a system detector.

Also, preferably, the system further comprises a user device comprising a graphical interface for displaying operations of the system and for altering system parameters. In one aspect, the system further comprises a read-out device for displaying output from the detector.

In another aspect, the system further comprises a positioning mechanism for restricting vertical movement of the at least one tip electrode. Preferably, the positioning mechanism is mounted to the target-facing end of the at least one tip electrode. However, the positioning mechanism may also be an integral part of the tip electrode.

The invention further provides a method comprising exposing a sample comprising a target and at least one non-target component to a focused electric field, wherein the focused electric field selectively alters the properties of the target. In one aspect, the target comprises a selected biological membrane and the non-target components comprise non-selected biological membranes. Exemplary targets include, but are not limited to, a population of cells, a single cell, an intracellular organelle, a vesicle, a liposome, a molecule, a group of molecules, a nucleic acid, protein, polypeptide, peptide; enzyme; carbon fiber; chemical reactant and a surface.

In one aspect, the target is suspended in a liquid comprising at least one non-target. In another aspect, the target is associated with a substrate. In a further aspect, the substrate comprises an array. In still a further aspect, the substrate comprises a microtiter dish. A plurality of targets may be localized at discrete locations on a substrate or in solution and separated from other targets by a physical barrier.

In one aspect, the electric field is provided by any of the tip electrodes described above.

In another aspect, the method comprises exposing each of a plurality of targets in a sample comprising a plurality of non-target components to a focused electric field. Preferably, each focused electric field is independently tunable. In one aspect, a plurality of tip electrodes, such as any of those described above, provide the focused electric fields. The plurality of targets may be exposed sequentially and/or in parallel to the plurality of focused electric fields. Each of the plurality of tip electrodes may be positioned over the well of a microtiter plate or over a spot on a substrate on which a target is located.

In one aspect, the target comprises a biological membrane and the exposing generates pores in the membrane. Thus, the method may be used to expose the target to an agent. In another aspect, exposure to the electric field and exposure to the agent are coordinated.

In a further aspect, the method comprises altering the condition(s) of a solution in which the target is bathed. For example, the method comprises the step of altering the pH, temperature, ionic strength, osmolarity, and/or viscosity combinations of a solution in which the target is bathed.

In one aspect, the focused electric field is provided by a tip electrode which may be coupled to a plate. The plate may comprise at least one channel in fluid communication with the lumen of the tip electrode. Additionally, or alternatively, the substrate may comprise at least one channel in fluid communication with the target through which the target may be exposed to an agent. In one aspect, the substrate comprises a plurality of channels in fluid communication with the target and a plurality of agents and/or buffer may be delivered sequentially or in parallel to the target from the plurality of channels.

The plurality of channels also may be used to expose the target to at least one fluid stream from the at least one target. In one aspect, the target is scanned across the at least one fluid stream by moving the target, moving the substrate, moving both the substrate and the target and/or by varying pressure at the at least one channel of the substrate.

The invention further provides a method comprising exposing a sample comprising a target and at least one non-target component to a focused electric field, wherein the focused electric field selectively alters the properties of the target and detecting the altered property. The method also may include the step of monitoring one or more parameters of the electric field and in one aspect, the method further comprises the step of altering a parameter of the electric field in response to detection of the altered property.

The method further may include the step of exposing a target to a fluid stream by delivering a fluid stream from a microfluidic channel outlet in proximity to the target. In one aspect, the fluid comprises an agent and delivery of the fluid stream is coordinated with exposure of the target to the electric field. Delivery of agent through a tip electrode may be facilitated through electrophoresis or electroosmosis.

In one aspect, the electric field induces a dipole in one or more target molecules.

In another aspect, the electric field causes one or more target molecules to stretch, move, bind, react, and/or denature.

In a further aspect, the target is a surface and the tip electrode delivers molecules for patterning the surface with a plurality of molecules, macromolecules, cells, or combinations thereof.

In one aspect, the target is a cell or cell structure (e.g., an organelle) and the agent is a label. In another aspect, the label interacts with an intracellular molecule or intra-organellar molecule to produce a detectable signal or reactant, and the method further comprises the step of detecting the detectable signal or reactant, thereby providing a means to determine the presence, absence and/or amount of the molecule.

In another aspect, the target is a cell or cell structure that is pre-loaded with half of a FRET pair and the method further comprises the step of exposing the target to the other half of the FRET pair during and/or after exposure to the electric field. Production of a FRET signal confirms pore formation.

The method may be used to transfer solutes from the medium outside a compartment defined by a membrane (e.g., such as a cell) into the compartment defined by the membrane. Alternatively, the method may be used to transfer solutes from the medium inside a compartment defined by a membrane (e.g., such as a cell) into a solution outside the membrane.

In one aspect, the agent may interact with an intracellular molecule, macromolecule, polymer ion, protein, polypeptide, peptide, or nucleic acid, to produce a detectable product, and the method further comprises detecting the detectable product. In another aspect, the method comprises the step of detecting a response of the compartment to the internalization of the agent. For example, detection may be performed by monitoring capacitance, voltametry, amperometry, CARS (coherent anti-stokes raman scattering), SERS (surface-enhanced raman scattering), phosphorescence, chemoluminescence, UV-VIS-IR absorption, quartz crystal microbalance, or surface plasmon resonance.

In a further aspect, the target is a cell of a selected type and the non-target is a cell of a different type. Alternatively, the target may be an organelle of a selected type while the non-target is an organelle of a non-selected type.

The invention also provides a method of screening for an agent that alters an interaction between a first intracellular component and a second intracellular component. The method comprises contacting a cell comprising the first intracellular component and the second intracellular component with the agent, exposing the cell to a focused electric field using any of the tip electrodes described above under conditions for generating pores in the cell, and detecting a change in the interaction. The exposing step may occur before, during and/or after the contacting step.

In one aspect, the first and/or second component is labeled and the method comprises detecting a change in a signal produced by one or both labels after the exposing.

In another aspect, the method comprises detecting the presence or absence of, or a change in, a reaction that occurs when the first and second component interact. For example, the first component may be an enzyme and the second component a substrate or co-factor. Interaction of the first and second component may be monitored by detecting the presence, absence or change in amount of reactants.

In a further aspect, the method comprises detecting the presence or absence of, or a change in a cellular or extracellular function or phenotype associated with the interaction of the first and second component.

In still a further aspect, the interaction comprises binding of the first and second component.

Exemplary first and second components are independently selected from the group consisting of an intracellular molecule, macromolecule, metabolite, polymer, protein (e.g., a receptor, ligand, enzyme, cytoskeletal protein, signaling protein, ion channel, organelle membrane protein, or cell membrane protein), polypeptide, peptide, nucleic acid, nucleobase, nucleotide, vesicle, cell membrane component, organelle and combinations thereof.

In one aspect, the agent is an agonist, antagonist or inhibitor of the first or second component.

In another aspect, the agent modulates a signaling pathway.

In a further aspect, the agent modulates a metabolic pathway.

In still another aspect, the first component is an intracellular receptor and the second component is a ligand which binds the intracellular receptor.

The invention further provides a method of screening for an agent that binds to an intracellular component. The method comprises contacting a cell comprising the intracellular component with a candidate binding agent, exposing the cell to a focused electric field using a tip electrode such as described above under conditions for generating pores in the cell, and detecting binding of the agent to the component. In one aspect, the agent and/or intracellular component are labeled and the method comprises detecting formation of a complex between the agent and the intracellular component. Alternatively or additionally, the method comprises detecting a phenotype associated with binding. In another aspect, the method comprises detecting a reaction produced with the intracellular component binds to an agent. In one aspect, the reaction comprises an increase in levels of a signaling molecule (e.g., such as $Ca^{2+}$, cAMP, and $K^+$). The intracellular component may include, but is not limited to, an an intracellular receptor, the cytoplasmic domain of a cell membrane molecule, or an enzyme.

BRIEF DESCRIPTION OF THE FIGURES

The objects and features of the invention can be better understood with reference to the following detailed description and accompanying drawings.

FIG. 3A is a close-up of one individual tip-electrode in this fashion and FIG. 3B illustrates the plate with a two-dimensional matrix of parallel tip-electrodes.

FIG. 4A shows tip-electrodes with uniform inner diameters and varying outer diameters, i.e., uniform, narrowing or expanding outer diameter. FIG. 4B shows tip-electrodes with a narrowing inner diameter and narrowing, uniform, or expanding outer diameters.

FIG. 5A shows an electrode plate with an aperture for receiving a single tip-electrode, FIG. 5B shows an electrode plate with apertures for a linear array of tip-electrodes. FIG. 5C shows an electrode plate adapted for a two-dimensional matrix array of tip-electrodes.

FIGS. 6B and 6C further illustrate an aspect of the invention in which tip-electrodes are spaced apart so that there center-to-center distance corresponds to the center-to-center distance in an industry standard microtiter plate to facilitate parallel electroporation in each of the wells of a microtiter plate.

FIG. 7A shows a suitable plate for electroporating a single spot of cells. FIGS. 7B-D show. suitable plates in the case where a plurality of spots are to be electroporated. FIGS. 7B and C also illustrate suitable plates for selectively electroporating individual wells of a cell container such as a microtiter dish. FIG. 7D also illustrates a cell container that would be suitable for electroporating a large population of cells, such as in a confluent culture.

FIG. 9A shows non-limiting examples of how the tip-electrode can be varied. The conducting part of the tip can be designed as a wire penetrating the wall of the housing defining the tip and connected on the outside to a ring plate (FIG. 9A), as a rod penetrating the tip wall on one (FIG. 9B) or both sides (FIG. 9C), as a wire or rod sticking down into the tip from the top (FIG. 9D), or the conducting part can be coated on the inside, and partly on the outside of the tip (FIG. 9E). The tip may also contain holes in the outlet region so the electric field can spread in three dimensions to enable electroporation of suspended cells (FIG. 9F). FIG. 9G illustrates how the design of the counter electrode can be varied. It can be shaped as a single or a plurality of wires or rods, as a cylinder where the tip-electrode is placed in the middle, as a ring-shaped wire with the tip-electrode in the middle or as a small plate electrode. FIG. 9H illustrates different embodiment in which a counter electrode is mounted in the cell plate instead of the electrode plate, either as a solid electrode or as a coated conducting layer on the cell plate.

FIG. 13A shows an aspect of the invention in which a stiff tip electrode is attached to or integrated with a flexible portion of the electrode plate. FIG. 13B shows an aspect of the invention in which the tip electrode is flexible and attached to or integrated with the electrode plate. FIG. 13C shows an aspect of the invention in which a positioning mechanism (e.g., such as a vertical bar) is provided which also provides an electrically conducting surface. FIG. 13D shows an aspect of the invention in which the tip electrode comprises an integrated positioning element at its tip. FIG. 13E shows an aspect of the invention in which a tip electrode comprises a detachable positioning element at its tip. FIG. 13F shows another exemplary positioning element according to the invention. FIG. 13G shows an aspect of the invention in which a positioning element is provided comprising an end with is tapered to form a tip.

FIGS. 14A-E show electroporation and internalization of fluorescein diphosphate (FDP) into PC12 cells situated 50 μm under a tip-electrode. FDP is not fluorescent until cleaved in the cytosol to fluorescein by phosphatases. The tip-electrode was filled with Hepes-saline buffer (pH 7.4) with 500 μM FDP. Cells were electroporated with 5×10 pulses, 3 mA, of 100 ms duration with a delay time of 100 ms between pulses. FIG. 14A is a brightfield image of the cell culture and FIG. 14B shows the same culture in fluorescence after electroporation. FIGS. 14C-E show simultaneous parallel electroporation of two spots of cells in the same cell culture. PC-12 cells were electroporated with 500 μm FDP in Hepes-saline buffer (pH 7.4) with a 4 mA pulse train of 20 pulses of 100 ms duration and 100 ms delay time between pulses. The distance between the two tip-electrodes and the cell culture were approximately 100 μm. FIG. 14C is a brightfield image of the cell culture; FIG. 14D is a fluorescence image of the culture and the target-facing end of the tip-electrodes prior to electroporation. FIG. 14E shows the fluorescence of the same culture after electroporation.

DETAILED DESCRIPTION

Figure 1:
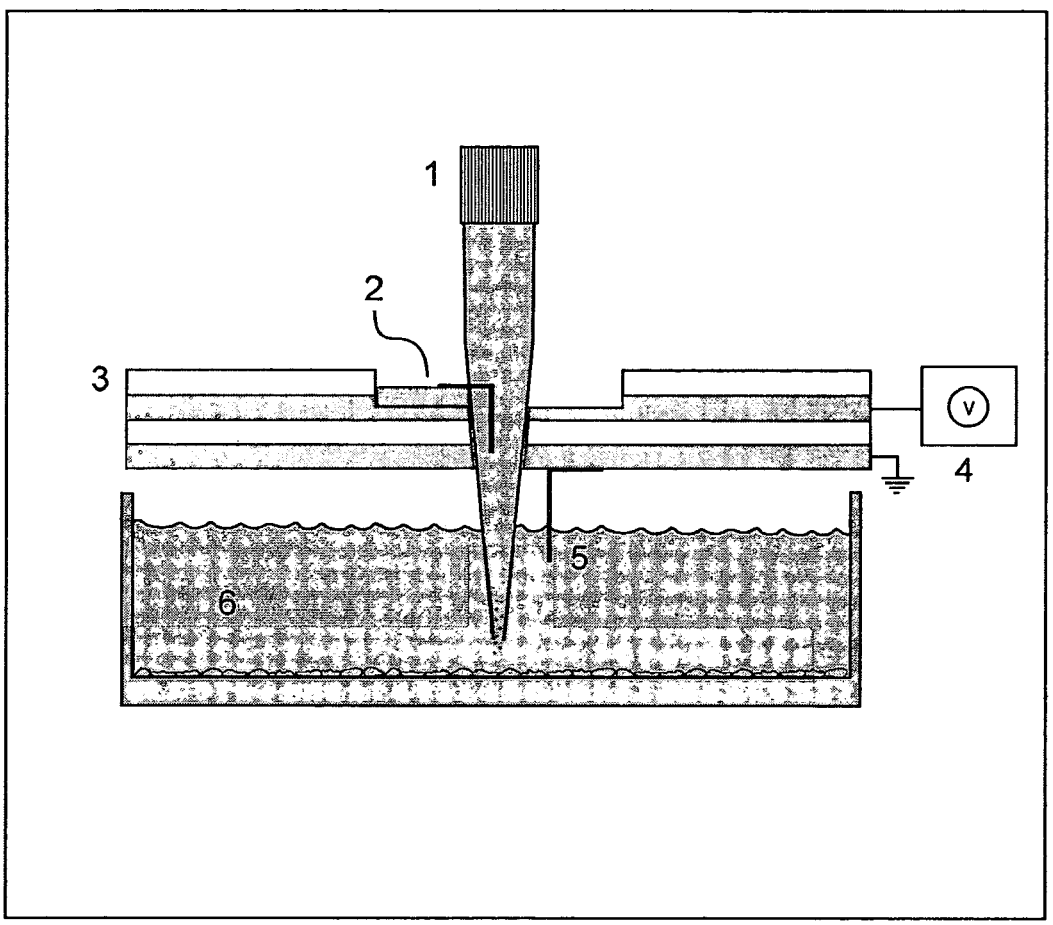
FIG. 1 is a representation of an electroporation system comprising tip-electrodes of one aspect of the invention. The system comprises an electrolyte-filled tip-electrode (1) having an internal electrode (2) in electrical contact with an electrode plate (3). The electrode plate is connected to a pulse generator (4) for delivery of voltage or current pulses through the tip-electrode and ground to a counter electrode (5). The tip-electrode is positioned in a cell bath (6) so the electrolyte solution contained in the tip is in contact with the solution in the cell bath.

The invention provides hollow-tip-electrodes for spatially localized delivery of substances to one or more biological targets present in a population comprising target and non-target molecules, macromolecules, and/or cells. The invention also provides electrode plates for receiving one or more of such tips, tip-electrode plates comprising electrode plates comprising one or more electrode tips, and systems comprising tip-electrodes and containers for containing one or more biological targets, e.g., such as molecules, macromolecules, and/or cells. The invention further provides methods for using such systems and components thereof. In one preferred aspect, the systems are used for spatially confined electroporation of cells and cell structures. The invention facilitates high throughput screening of agents (e.g., such as drugs) that act on intracellular targets.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a protein" includes a plurality of proteins.

As used herein, a "microchannel" refers to a groove in a substrate comprising two walls, a base, at least one inlet and at least one outlet. In one aspect, a microchannel also has a roof. The term "micro" does not imply a lower limit on size, and the term "microchannel" is generally used interchangeably with "channel". Preferably, a microchannel ranges in size from about 0.1 μm to about 1000 μm, more preferably ranging from, 1 μm to about 150 μm.

As used herein, "scanning of a target relative to one or more channels in a microfluidic substrate" refers to exposure of the target to a plurality of fluid streams from at least one channel in the substrate. This may be achieved by moving a target past one or more channel outlets in a stationary substrate providing such streams or by moving the substrate relative to a stationary target so that it is exposed to streams from one or more channel outlets of the substrate. Scanning may also be achieved by moving both the substrate and the target. Exposure to a plurality of fluid streams from a single channel may be achieved by providing different fluid streams (e.g., comprising different agents, or different doses of the same agent, or alternating buffer flow and flow of fluid stream containing an agent, or some combination thereof) from the single channel and/or by intermittently stopping the flow of fluid from an outlet of the channel in proximity to the target. In an embodiment where the target is stationary, scanning can be done by varying pressure at one or more channels. Combinations of the above scanning mechanisms may be used during a scanning process and variations of such combinations are obvious and encompassed within the scope of the invention.

"Protein", as used herein, means any protein, including, but not limited to enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues. The terms "polypeptide" and "protein" are generally used interchangeably herein to refer to a polymer of amino acid residues.

As used herein, "a polypeptide" refers to a plurality of amino acids joined by peptide bonds. Amino acids can include D-, L-amino acids, and combinations thereof, as well as modified forms thereof. As used herein, a polypeptide is greater than about 20 amino acids. The term "polypeptide" generally is used interchangeably with the term "protein"; however, the term polypeptide also may be used to refer to a less than full-length protein (e.g., a protein fragment) which is greater than 20 amino acids.

As used herein, the term "receptor" refers to a macromolecule capable of specifically interacting with a ligand molecule. Receptors may be associated with lipid bilayer membranes, such as cellular, golgi, mitochondria, or nuclear membranes, or may be present as free or associated molecules in a cell's cytoplasm or may be immobilized on a substrate.

As used herein, the term "in communication with" refers to the ability of a system or component of a system to receive input data from another system or component of a system and to provide an output response in response to the input data. "Output" may be in the form of data, or may be in the form of an action taken by the system or component of the system. For example, a processor "in communication with a scanning mechanism" sends program instructions in the form of signals to the scanning mechanism to control various scanning parameters as described above. A "detector in communication with a measurement chamber" refers to a detector in sufficient optical proximity to the measurement chamber to receive optical signals (e.g., light) from the measurement chamber. A "light source in optical communication" with a target refers to a light source in sufficient proximity to the target to create a light path from the target to a system detector so that optical properties of the target can be detected by the detector.

As used herein, "a measurable response" refers to a response that differs significantly from background as determined using controls appropriate for a given technique.

As used herein, the term "electrode" refers to a device that transmits or conducts electric signals.

As used herein, a tip electrode "at close distance to a target" or in "proximity to a target", means that the outlet end of the tip-electrode is placed at a suitable distance to a target (e.g., a cell or cellular structure) to transiently change the electrical properties of the target (e.g., change the dieletric properties of and create pores in a cell membrane). Preferably, said close distance is less than 1 mm.

As used herein, the term "electrolyte solution," refers to the solution within a tip electrode. The term is used without limitations to the actual composition or ionic strength of the electrolyte.

As used herein, the term "bath solution" refers to the solution or medium surrounding a cell or cell structure.

As used herein, an "electric field focused on at least one target" or "electric field focused on at least one cell or cellular structure", means that the electric field is focused on the one or several target/cell(s)/cellular structures whose electrical properties are to be altered essentially without affecting any surrounding targets/cells/cellular structures.

The expression "a strength sufficient to obtain dielectric breakdown and pore formation," means that the electric field is essentially exactly what is needed for electroporation.

As used herein, a "highly focused" electric field refers to a spatially confined electric field which most often is nonuniform in intensity in either the axial or lateral dimensions.

As used herein, "tunable" electric field refers to an electric field which can be altered with respect to polarity, phase, frequency, amplitude (voltage or current) or time.

As used herein, "spatially confined" electroporation refers to electroporation of selected domains such as a group of cells on a surface or in solution where other groups of cells in the same solution or on the same surface are untreated.

As used herein, the term "biological membrane" refers to a lipid bilayer surrounding a biological compartment, and includes the membranes of natural or artificial cells (e.g., such as liposomes), membrane vesicles or portions thereof. The term "biological membrane" encompasses a membrane surrounding an entire cell (e.g., a cell membrane), a portion of a cell, an artificial cell, or a portion of an artificial cell, and further encompasses a membrane of an organelle.

As used herein, the term "glass" refers to any of a large class of materials that are typically made by silicates fusing with, but not limited to, boric oxide, aluminum oxide, or phosphorous pentoxide.

As used herein, a "substantially planar substrate or plate comprising a nonplanar element for altering electrical properties of a target refers to substrate which comprises an element whose surface is elevated or depressed relative to the surface of a substrate, wherein the element comprises at least two points that lie in different planes relative to the surface of the substantially planar substrate and relative to each other.

Targeting and Delivery Systems

Systems of the invention comprises at least one tip-electrode and a container for receiving a target to be selectively exposed to an electric field produced by a tip-electrode for altering properties of the target. For example, a tip-electrode of the invention can be used to alter the dielectric properties of a cellular or intracellular membrane in its proximity, thereby creating pores in the membrane.

Further, tip-electrodes of the invention also provide a delivery device for delivering agents or altering conditions of a solution in which a target is bathed (e.g., such as pH, ionic strength, etc). As shown in FIGS. 2A-C, in one aspect, tip-electrodes have properties of both a pipette tip and of an electrode. By combining these properties, generation of an electric field by the electrode within the tip-electrode and agent delivery can be coordinated in a way that optimizes exposure to the electric field (for example the creation of pores in a cell membrane) and interactions with the agent (e.g., agent internalization through the pores).

In one preferred aspect, the system further comprises an electrode plate for receiving at least one tip-electrode. The electrode plate, in combination with a plurality of tip-electrodes, may provide an array of tip-electrodes for simultaneous or sequential exposure (or some combination of such exposure) to an electrical field and/or agent.

In operation, the device is coupled to a power supply for delivering current or voltage, and preferably to a pump for enabling precise delivery of amounts of agents. See, e.g., FIG. 1. In addition, robotics for automated pipetting and a plate-reading system for read-out can be coupled to the device for optimal efficiency. The components of systems of the invention are described further below.

Tip-electrodes

A tip-electrode comprises a housing defining a lumen for delivering an agent and/or for altering a condition in the solution environment of a target. The housing may be in the form of a short capillary, a small pipe or a pipette tip. Suitable housing materials include, but are not limited to: glass, fused silica, plastic, ceramic, elastomer, polymer, metal, or any other suitable, preferably non-electrically-conducting material. In one aspect, the tip-electrode housing comprises a target-facing end comprising an opening through which an agent may be delivered. The tip-electrode further comprises a solid electrically conducting surface for exposing a target in proximity to the target-facing end of the tip-electrode to an electric field.

Preferably, the lumen of the tip-electrode comprises a non-solid electrically conductive medium. The non-solid conducting medium may be a liquid, a paste, a polymer, a semi-solid medium such as a gel, a resin, and the like. In one aspect, the non-solid conducting medium is an electrolyte solution. In another aspect, the medium comprises a physiological buffer. In one aspect, the medium comprises one or more agents, which may be delivered through the opening of the target-facing end of the tip-electrode to a target. Injection, or filling, of tip-electrodes can be achieved using standard techniques. For example, the electrolyte solution may be injected into the tip from the opening in the target-facing end of the housing or from a back opening at the end of the housing distal from the target-facing end ("the receiving end"). Gravity flow, pressure-based pumping or some other means may be used.

Preferably, delivery of an agent is synchronized with delivery of a current or voltage conducted from the electrically conducting surface through the medium.

The electrically conductive surface may be an element removable from the housing or can be an integral component of the housing. See, e.g., FIG. 9D. In one aspect, the electrically conductive surface of the tip-electrode is in the form of a rod, cylinder, wire, or other electrically conducting structure conformed to fit into the lumen of the tip-electrode. For example, the electrically conductive structure may be inserted into the receiving end of the housing and in contact with the electrically conductive medium in the lumen of the housing. The electrically conductive surface may be coupled to a power supply through one or more connections at the receiving end for transmitting a voltage or current pulse through the electrically conductive medium. An opening at the receiving end may also be in communication with a liquid dispensing system for synchronizing generation of an electric field by the tip-electrode with delivery of one or more agents from the target-facing end of the housing. However, the electrically conducting structure may be placed anywhere on the inside of the lumen of the housing of the tip-electrode.

Figure 9:
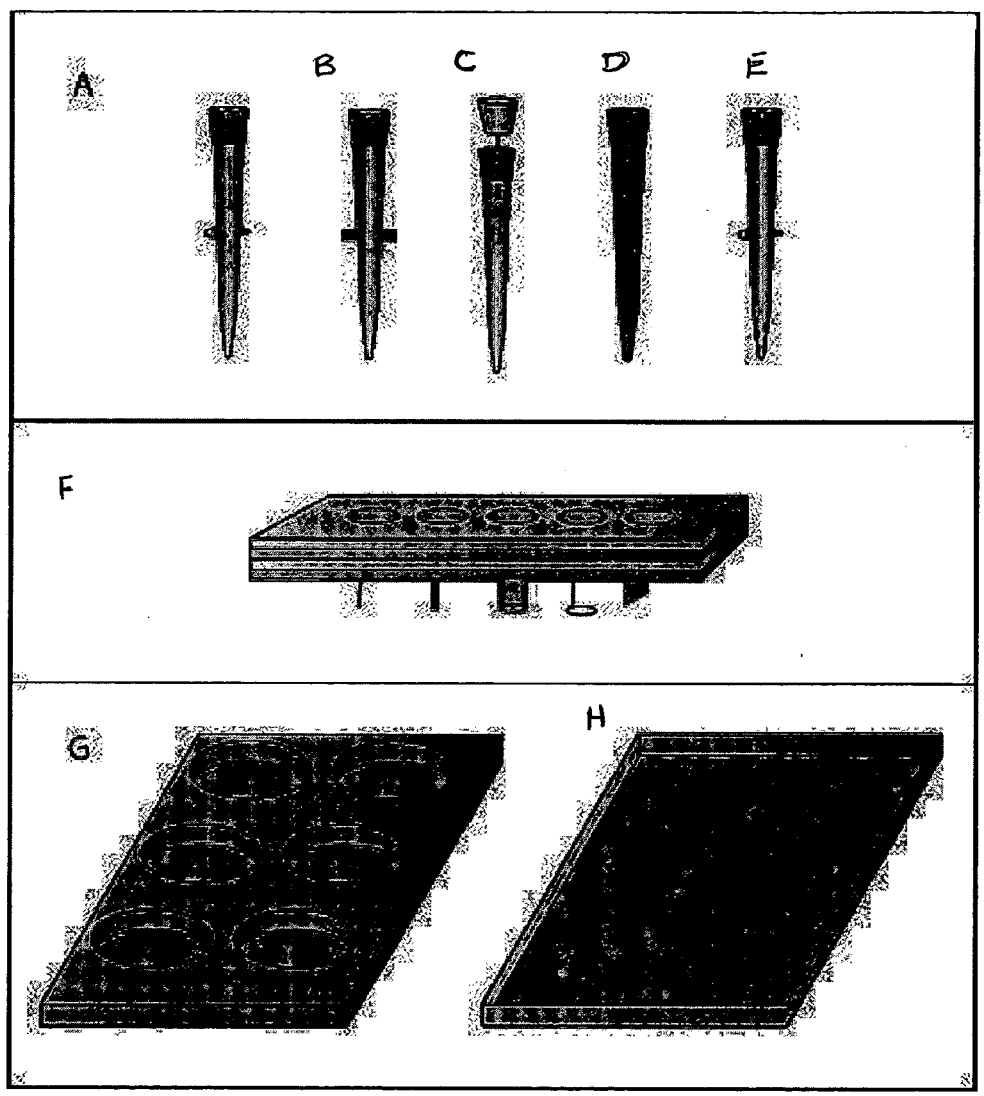
FIGS. 9A-H illustrate how the different components of an electroporation system of the invention can be altered in design and in function.

In another aspect, the conducting part of the tip also can be a wire penetrating the wall of the housing. For example, the electrically conducting structure may be a wire connected on the outside of the housing to a ring plate (FIG. 9A), or a rod penetrating the wall of the housing on one (FIG. 9B) or both sides (FIG. 9C).

However, in a further aspect, the electrically conducting surface of the tip-electrode is part of the housing itself. For example, the inner walls of the housing may comprise a surface that is at least partially conducting and is in contact with the electrolyte solution. See, e.g., FIG. 9E.

Electrode surfaces on the housing may be provided in a number of non-limiting ways. For example, a housing comprising a conducting material may be coated with an insulating film on the outside. It is also possible to coat the inside of the a housing comprising non-conducting material with any conducting material, not limited to metals or conducting polymers. The inside of the housing may be entirely or partially coated with a conducting polymer. In one aspect, the target-facing end of the housing may be coated. An electrical connection to the housing is transported through the conducting surface of the housing and through the electrolyte solution delivering a focused electric field to a target.

The housing may comprise a varying outer and/or inner diameter, providing a tapered target-facing end. Alternatively, the housing can comprise a cylindrical second end. It is possible to use any design at the target-facing end and variations in inner and outer diameter of the housing which optimizes the electric field generated by the tip-electrode in the way most suitable for a particular target. For example, the design of the tip end may be modified of the number and size of cells to be electroporated by the tip-electrode.

Figure 4:
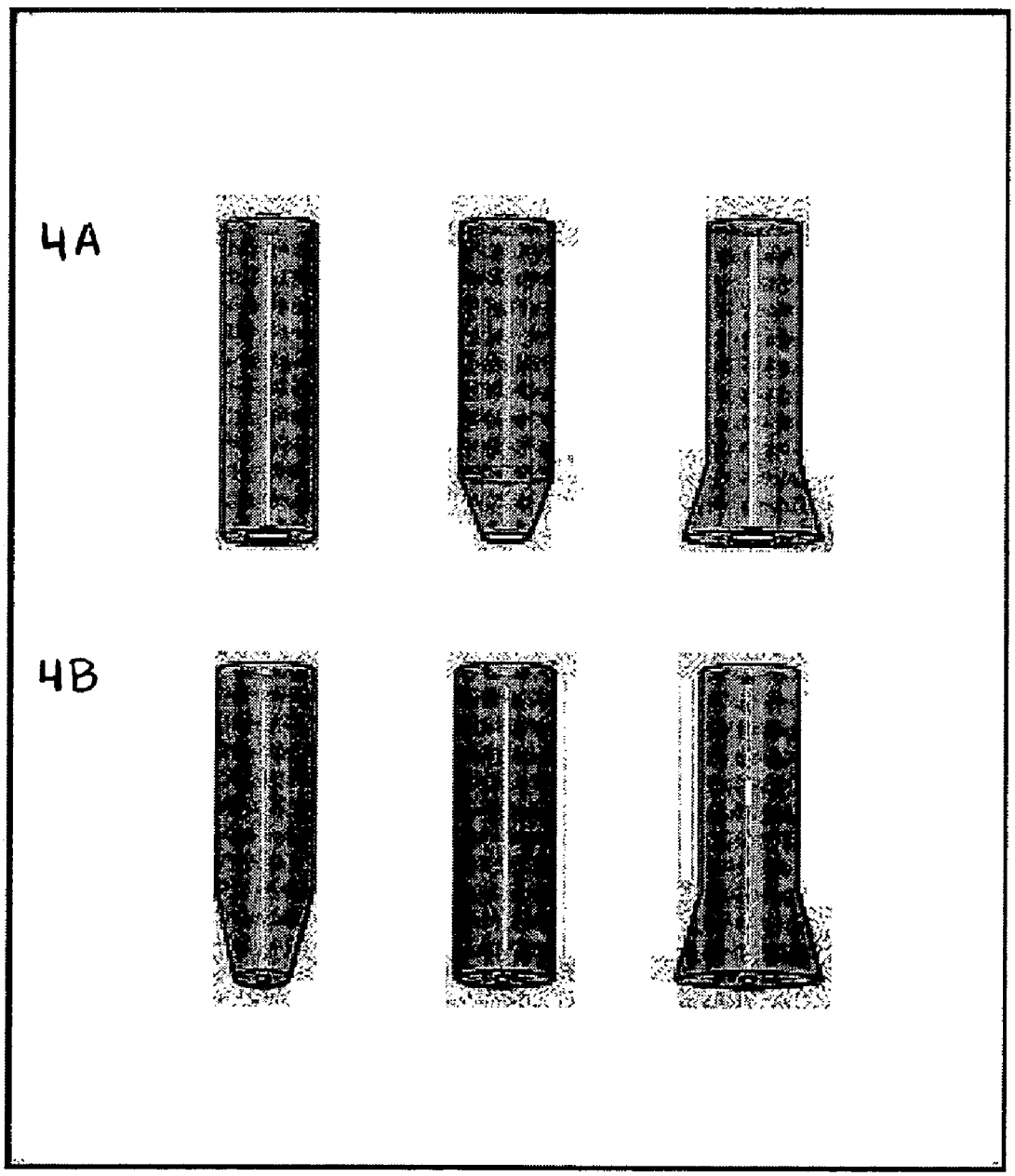
FIGS. 4A and 4B show non-limiting examples of how the geometry of the end of the tip-electrode in proximity to cell(s) can be varied.

FIG. 4 shows non-limiting examples of how the geometry of the target-facing end of the tip-electrode can be varied. The top row shows tip-electrodes with uniform inner diameters and varying outer diameters, i.e., uniform, narrowing or expanding outer diameters. The bottom row shows tip-electrodes with narrowing inner diameter and narrowing, uniform, or expanding outer diameters.

Preferably, the length of a tip-electrode is less than about 50 cm, less than about 25 cm, less than about 10 cm, less than about 5 cm, less than about 1 cm, less than about 500 µm, less than about 200 µm, less than about 100 µm, 10 µm, and even less than about 1 µm depending on application. Generally, the diameter of the opening at the target-facing end of a tip-electrode is from about one nanometer to several thousand micrometers, such as from 50 nm to 5000 µm. For electroporation of small populations of cells it is often suitable to use tips with an inner diameter between 50 to 2000 µm and an outer diameter between 60 and 5000 µm, whereas for single-cell and organelle electroporation, tips with an outer diameter of 0.03-50 µm and a inner diameter of 0.025-49 µm are suitable.

Tip-electrodes can be generated using a variety of fabrication methods. Tip-electrodes can, for example, be generated using standard puller devices equipped with a filament to melt an elongated starting material and to stretch the material to form a tip having the appropriate dimensions. For materials with very high melting temperatures such as quartz or fused silica, puller devices equipped with a carbon dioxide laser or Tantalum filaments are preferably used. Such fabrication methods are ideal for producing small numbers of nanoelectrodes. Alternatively, chemical or flame etching, chemical or non-chemical vapor deposition processes, thermal growth, polymerization techniques such as electropolymerization or ion implantation can be used to microfabricate a tip of suitable dimensions. In certain aspects, discussed further below, tip-electrodes are fabricated as an integral component of an electrode plate.

Tip-electrodes of the invention can be used for intracellular delivery of one or more membrane-impermeable agents. An electric pulse applied across a tip-electrode gives rise to a small, focused and tunable electric field outside the terminus of the tip-electrode. When the tip-electrode is placed at a suitable distance from a membrane, such as a cell membrane or a membrane of an intracellular organelle, this electric field is sufficient to cause pore formation in the membrane.

The electric field created at the outlet of an electrolyte-filled tip-electrode can be estimated by using the solution to the electrochemical problem of calculating the potential change in solution in front of a circular disc electrode in an insulating plane with constant current density (Nanis and Kesselmann, *J. Electrochem. Soc.* 118: 454-461, 1971). The magnitude of the electric field extending out in the solution along the axis of symmetry of the tip-electrode is given by:

$$E(Z, \Psi) = \frac{\Psi}{L_c}\left[\frac{Z}{[1+(Z)^2]^{\frac{1}{2}}} - 1\right] \quad (3)$$

Where Z is the dimensionless distance from the outlet of the tip-electrode, z/a, where z is distance from the outlet and a is the tip-electrode radius. $\Psi$ is the applied potential in volts and $L_c$ is the length of the tip-electrode. This equation can be integrated to find the potential drop along the cylindrical axis outside the tip-electrode of:

$$V(Z) = \frac{a\Psi}{L_c}\left((Z^2+1)^{1/2} - Z\right) \quad (4)$$

The electric field strength from equation 3 can be inserted in equation 1 for calculations of the transmembrane potential over the cell membrane.

By varying the dimensions of the tip-electrode, or electric field parameters, the area affected by the electric field can be altered, and thus, for cellular applications, the number of cells targeted or exposed to the electric field and delivery of liquid in the tip-electrode (and therefore agents in the tip-electrode) can be controlled. Thus, a single cell, a plurality of cells, or a large population of several million cells can be targeted. The tip may also contain holes in the portion of the tip proximal to the target-facing end so the electric field can spread in three dimensions to enable electroporation of suspended cells. See, e.g., FIG. 9F.

In one preferred aspect, tip-electrodes are in electrical communication with one or more counter electrodes. The counter electrode may be moveable relative to the tip-electrode, e.g., in two, or three dimensions. In another aspect, the tip-electrode is moveable relative to the counter electrode. In still another embodiment, one or both tip-electrode and counter electrode are movable relative to a target. In a further embodiment, the counter electrode is in a fixed relationship with respect to the tip-electrode.

FIG. 9B illustrates non-limiting examples of how the design of the counter electrode can be varied. It can be shaped as a single or a plurality of wires or rods, as a cylinder where the tip-electrode is placed in the middle, as a ring-shaped wire with the tip-electrode in the middle or as a small plate electrode. FIG. 9C illustrates a counter electrode of another aspect of the invention, mounted in a container for containing targets for electroporation/agent delivery. The electrode may be provided as a discrete element within the container or as a coated conducting layer on a plate for containing targets such as cells.

Electrode Plates and Tip Arrays

The invention further provides an electrode plate for receiving one or more tip-electrodes. Tip-electrodes can be detachable from, or integrated as part of the electrode plate. Electrode plates provide a means to interface the tip-electrodes with macroscale devices such as power supplies, fluid delivery systems, pumps, and the like. In one aspect, an electrode plate can constitute interface between the tip-electrodes and the pulse generator. An electrode plate can conduct the same current/potential to all tip-electrodes in the system or address each tip-electrode individually.

In one aspect, an electrode plate comprises a plurality of tip-electrodes for targeting multiple targets simultaneously and/or for sequentially targeting a single target (e.g., by moving the electrode plate so that a target is exposed in sequence to a plurality of tip-electrodes).

In one preferred aspect, a plurality of tip-electrodes are arranged in a single row as a linear array. In another aspect, the plurality of tip-electrodes are arranged in a plurality of rows forming a two dimensional matrix. Generally, tip-electrodes may be arranged on an electrode plate in any manner that facilitates exposing one or more targets to electric fields and/or agents in a spatially confined and highly focused manner. In one aspect, tips are arranged to generate electric fields focused on spots at which targets are localized. For example, the tips may be arranged on the electrode plate so that the center-to-center distance between tips corresponds to the center-to-center distance of an industry standard microtiter dish. Other suitable arrangements based on the structure of a target container, e.g., such as a petrie dish, multi-well container, and the like, may be configured.

Since the distance between the target-facing ends of the tip electrodes can be very short, just a few micrometers, high spatial resolution of different targets may be achieved.

FIG. 2B illustrates a linear array of tip-electrodes aligned for parallel electroporation of targets, such as cells, in a plurality of wells/spots in a target container. FIG. 2C illustrates a two-dimensional matrix array of tip-electrodes for electroporation of a plurality of cells contained in plurality of wells or spots of cells. Numerals in A, B, and C show a modular form of tip-electrodes and electrode plate where components are detachable from each other. Thus, a pipette tip (1); electrically conducting structure (the electrode component of the tip-electrode); and mounting rack or plate (3) for receiving a mounting rack for a plurality of tip-electrodes may be assembled so that different types of tip-electrodes may be used with different electrode plates. Different electrode plates may be used with one or more different types of tips and different configurations of electrode structures may be used with a single type of housing for a tip-electrode.

If detachable tip-electrodes are employed, an electrode-plate can provide vertical alignment of the tip-electrodes to a specific height above a target-containing surface. The electrode plate can also harbor one or several counter electrodes. The design of the electrode plate may vary depending on the number of tip-electrodes and application. For detachable tip-electrodes, the electrode plate can be designed as shown in FIGS. 5A-C, with different layers of conducting and insulating materials.

Figure 2:
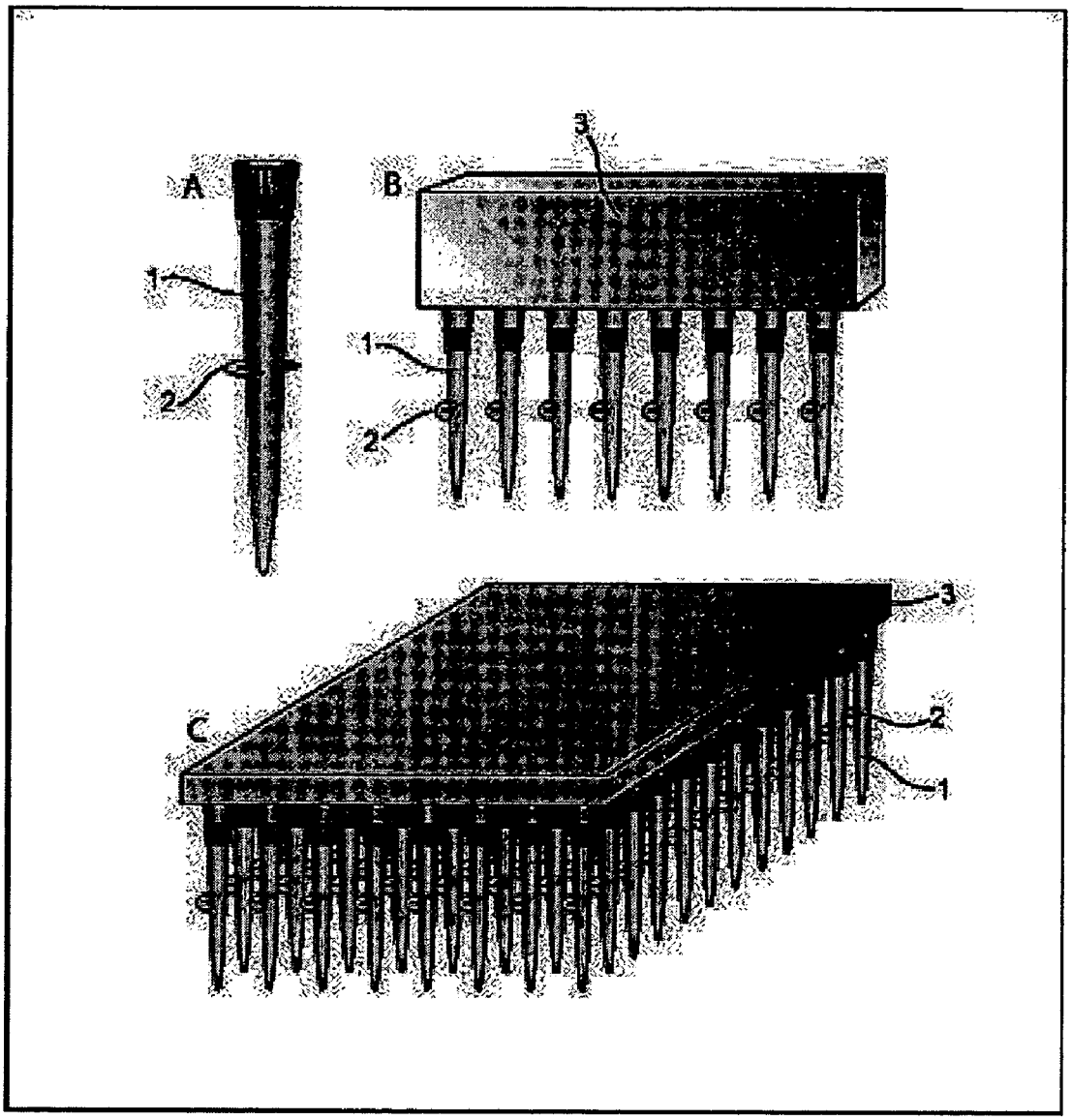
FIG. 2A shows a solitary tip-electrode for localized electroporation and internalization of agents in cells in a well of a microtiter plate or at a discrete location or "spot" in a cell culture container, such as a petrie dish, of one aspect of the invention.
FIG. 2B illustrates a linear array of tip-electrodes aligned for parallel electroporation of cells in a number of wells or spots.
FIG. 2C illustrates a two-dimensional matrix array of tip-electrodes for electroporation of a plurality of cells contained in plurality of wells or spots.
Figure 5:
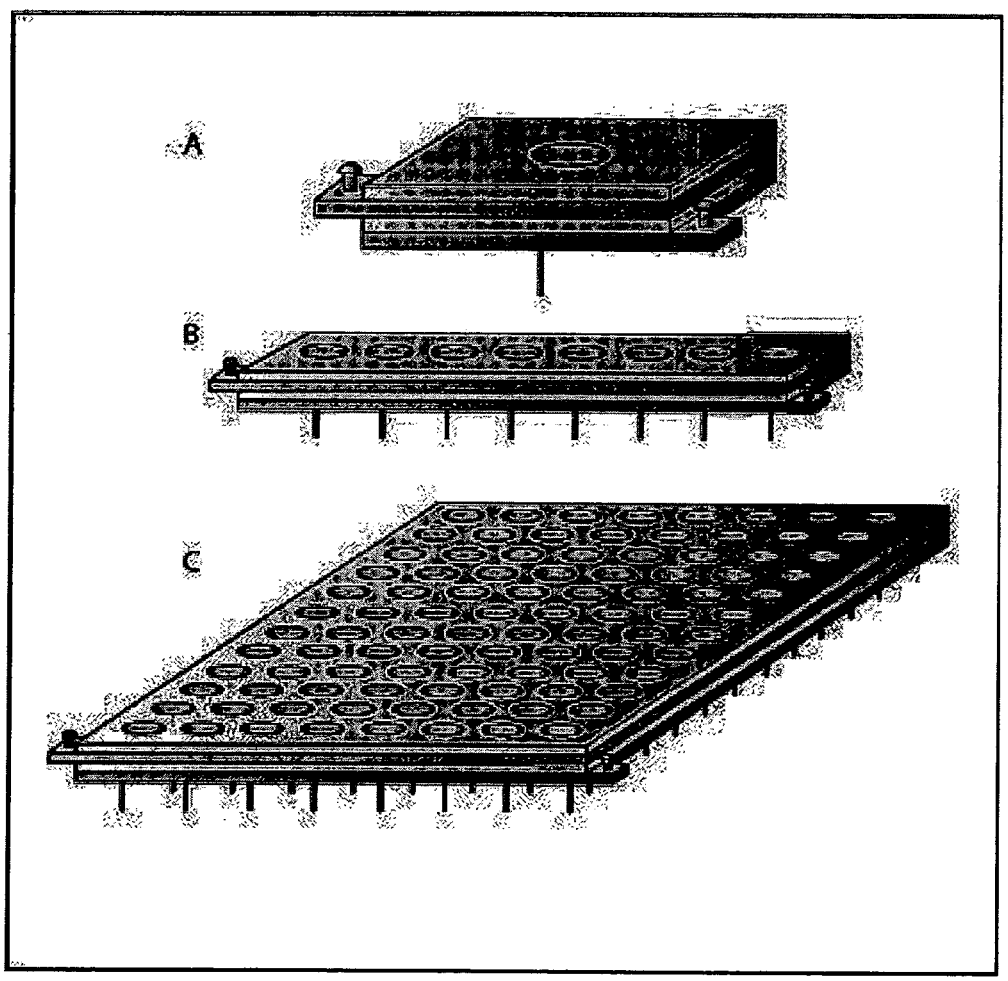
FIGS. 5A-C show the electrode plate for receiving tip-electrodes as shown in FIG. 2. In the embodiment shown in the Figure, the tip-electrodes can be detached from the plate.

FIGS. 5A-C show the electrode plate for receiving the tip-electrodes shown in FIG. 2 and exemplified for detachable tip-electrodes. FIG. 5A shows an electrode plate with an aperture for receiving a single tip-electrode. FIG. 5B shows an electrode plate with apertures for a linear array of tip-electrodes and FIG. 5C shows one for a two-dimensional matrix array of tip-electrodes. The electrode plate can be designed with any number of apertures desired and at any desired center-to-center distances, for example, to fit microtiter plates with various numbers of wells. The two kinds of layers of the electrode plate (conducting and insulating) and a counter electrode, can be fabricated in any kind of materials as long as their basal characteristics, i.e., having an insulating and conducting layer respectively, are fulfilled. The number of counter electrodes varies with application. The number usually correlates to the number of wells/targets to be exposed to an electric field (e.g., electroporated) and not to the number of tip-electrodes. For parallel electroporation of cells or cellular structures in separated wells, each tip-electrode is preferably provided with one counter electrode. For electroporation of two or more spots on a surface in one cell-containing reservoir, several tip-electrodes can operate against one or a few counter electrodes held at ground. Consequently, the application determines the number of counter electrodes that needs to be provided.

The electrode plate also contains contacts at the conducting layers for coupling to a current or voltage generator, illustrated by two screws.

Non-limiting examples of different substrate materials that can be used for the conducting layer of the plate include crystalline semiconductor materials (e.g., silicon, silicon nitride, Ge, GaAs), metals (e.g., Al, Ni), glass, quartz, crystalline or amorphous insulators, ceramics, plastics, other polymers (e.g., a fluoropolymer, such as Teflon®, polymethylmethacrylate, polydimethylsiloxane, polyethylene, polypropylene, polybutylene, polymethylpentene, polystyrene, polyurethane, polyvinyl chloride, polyarylate, polyarylsulfone, polycaprolactone, polyestercarboniate, polyimide, polyketone, polyphenylsulfone, polyphthalamide, polysulfone, polyamide, polyester, epoxy polymers, thermoplastics, and the like), other organic and inorganic materials, and combinations thereof.

Microfabrication techniques are ideal for producing very large arrays of electrode devices. For example, electrode devices comprising tips-electrodes can be manufactured by direct processing of a conducting solid-state material. Suitable solid-state materials include, but are not limited to, carbon materials, indium tin oxide, iridium oxide, nickel, platinum, silver, or gold, other metals and metal alloys, solid conducting polymers or metallized carbon fibers, in addition to other solid state materials with suitable electrical and mechanical properties. In one aspect, the electrode device comprises an electrically conductive carbon material, such as basal plane carbon, pyrolytic graphite (BPG), or glassy carbon.

In one aspect, for creating nanoscale devices, arrays are constructed on a doped semiconductor substrate by nanolithography using scanning STM or AFM probes. For example, metal clusters can be deposited either from a solution or by field evaporation from a Scanning Tunneling Microscope/Atomic Force Microscope (STM/AFM) tip onto such a substrate. The surface of the semiconductor can be oxidized so that substantially all of the surface is insulated except for tips protruding from the surface which are in contact with cells, thus minimizing electrode noise.

Electrode plates comprising tip-electrodes may also be fabricated by chemical or flame etching, vapor deposition processes, lithography and the like.

In a further aspect of the invention, the substrate comprises a non-electrically conducting material into which holes or apertures are bored, e.g., by laser light, electrical discharges or lithography-based nanofabrication techniques such as e-beam lithography, or by drilling or blasting. The apertures are filled with electrically conducting media and preferably a solid state conducting material, such as carbon fibers or electrically conducting polymers or metals. In one aspect, the substrate is coated with an electrically conducting material (e.g., such as a metal coating), and the rims of the apertures are raised to form tapered tips for insertion into cell membranes. In another aspect, only the raised rims of the apertures are electrically conducting. In a further aspect, only the cell-contacting surfaces of the apertures are electrically conducting.

Figure 6:
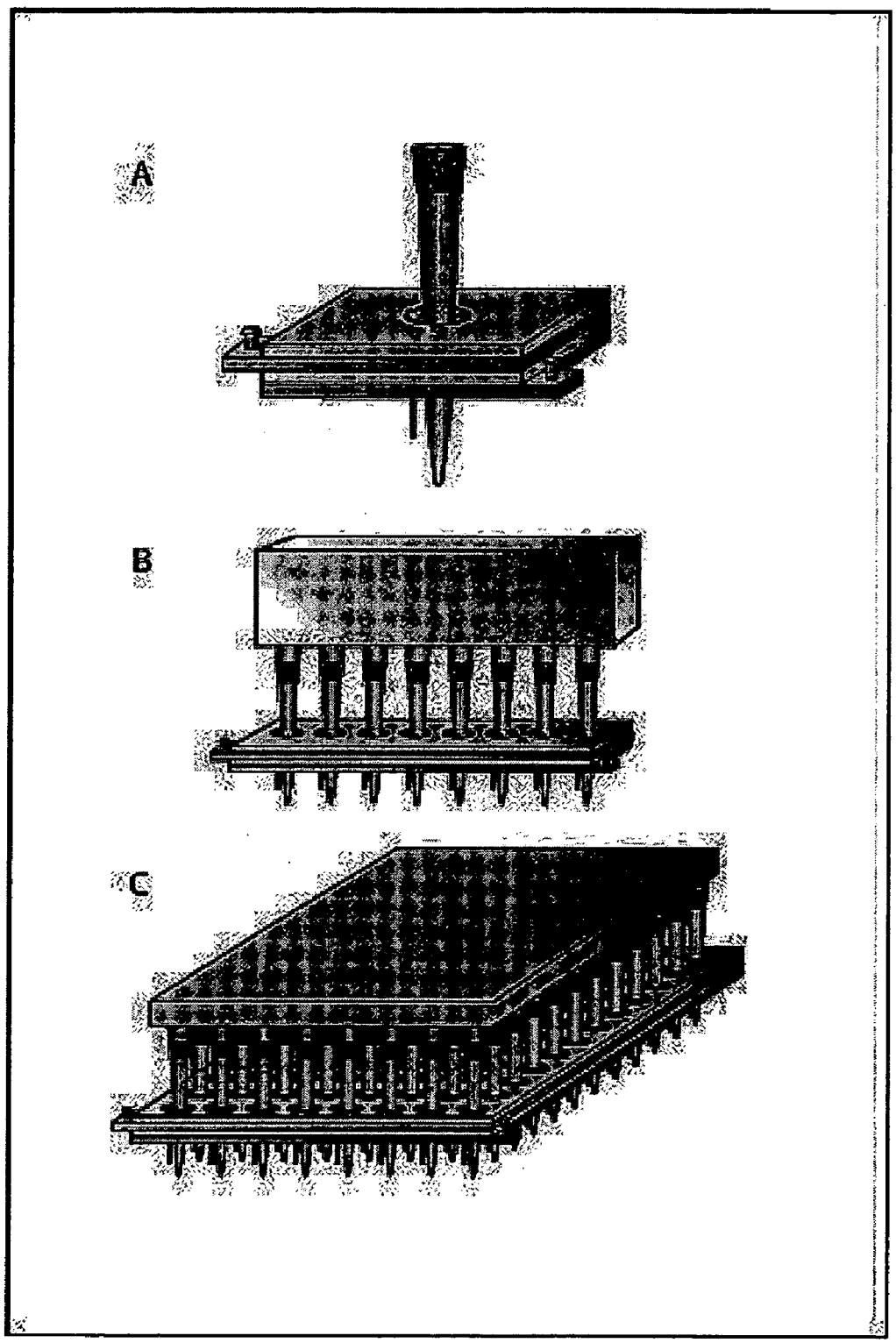
FIGS. 6A-C illustrates tip-electrodes mounted in an electrode plate of one embodiment of the invention for a single (FIG. 6A), a few (FIG. 6B), and a plurality of tip-electrodes (FIG. 6C).

Removable tip-electrodes inserted in an electrode plate are illustrated in FIGS. 6A-C for a single, a linear array and a two-dimensional matrix of tip-electrodes. FIGS. 6A-C illustrate tip-electrodes mounted in the electrode plate for a single (A), a few (B), and a plurality of tip-electrodes (C). FIGS. 6B and 6C illustrate electroporation in individual wells for each tip-electrode.

Figure 3:
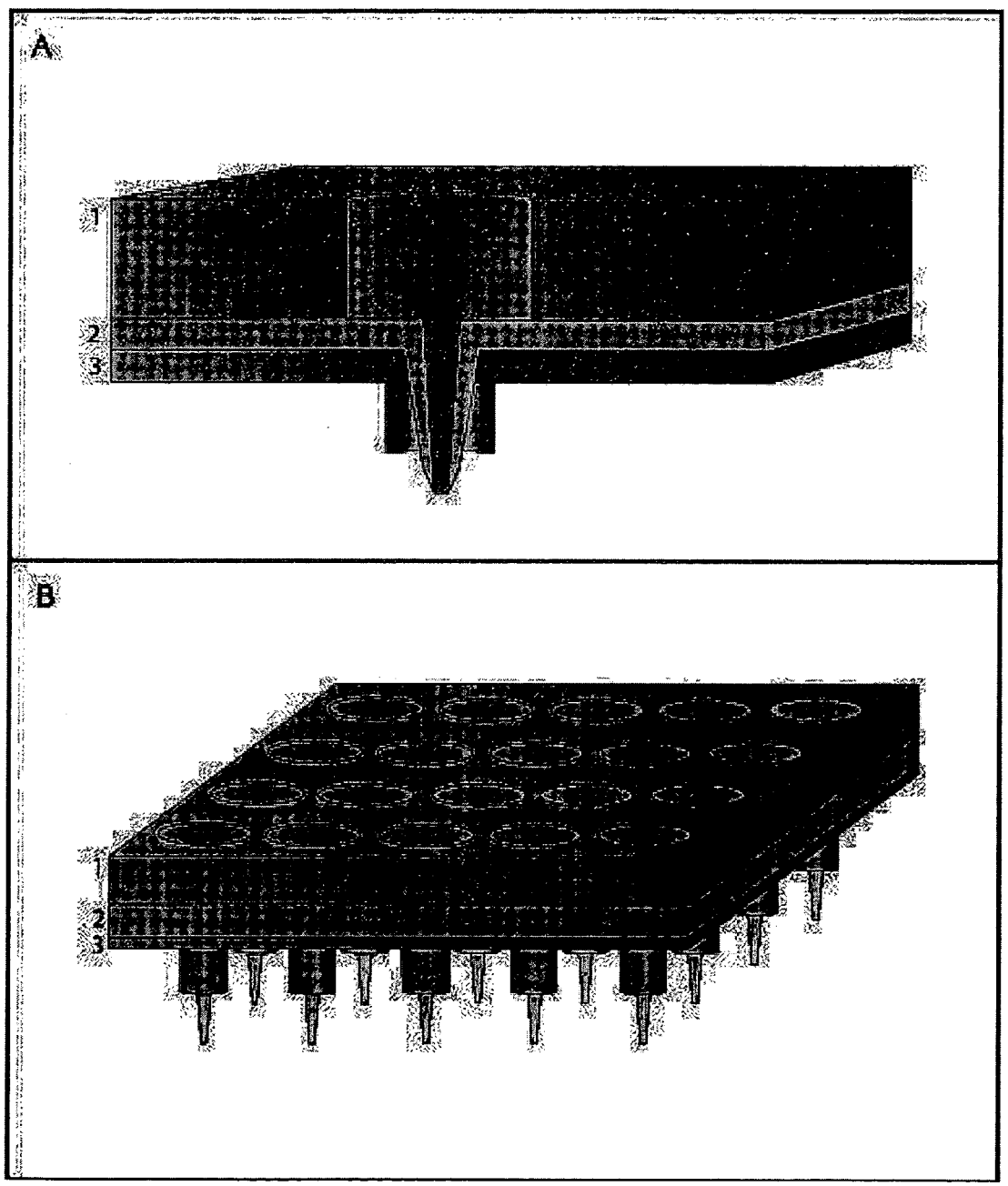
FIGS. 3A and 3B show an alternative design of the tip-electrodes where a plurality of tip-electrodes are molded in parallel in one plate. In one aspect, the plate consists of three different layers where layer (1) contains wells that act both as electrodes and electrolyte reservoirs and are made at least in part in a conducting material; layer (2) comprises a non-conducting layer with parallel tips corresponding to the wells in (1), and layer (3) is a counter electrode layer, here illustrated with individual circular counter electrodes corresponding to each tip-electrode.

A different embodiment is shown in FIGS. 3A-C. As shown in the Figure, a desired amount of parallel tip-electrodes may be manufactured as a single unit comprising a substantially planar plate with nonplanar elements fabricated thereon, the nonplanar elements forming tip-electrodes. The plate can be separated into different layers, as illustrated in the Figures.

In one aspect, the top layer of the plate contains a reservoir for an agent to be delivered to a target. Preferably, the reservoir comprises an electrically conducting surface or structure. The inner walls of the reservoir can be made from a conducting material so that entire reservoir acts as electrode, or the electrode can constitute a wire, rod or other type of electrically conducting structure, exposed in each well. The second layer comprises regions, preferably spaced at regular intervals, which are elevated above the rest of the plate forming protrusions, or tips, having openings centered above each reservoir in the first layer. These elevated regions comprise inner walls defining lumens which communicate with the reservoirs. Preferably, the lumens comprise an electrically conductive medium for transmitting voltage or current from the electrode and agent-containing reservoirs. More preferably, the ends of the nonplanar elements distal from the plate are tapered to facilitate localized delivery of agent from the reservoir.

As shown in FIGS. 3A-C, a third layer can be added to provide a counter electrode. In one aspect, each nonplanar element forming a tip-electrode includes a counter electrode layer. Such an arrangement is suitable, for example, tips are used to provide electric fields to individual wells of a microtiter dish, e.g., to perform electroporation. Alternatively, one or a few counter electrodes may be provided for electroporation of several spots or locations, e.g., in one confluent cell culture. In this aspect, the counter electrode can be positioned in the bottom of a target container which contains multiple nontarget elements (e.g., nontarget cells) along with one or more target elements (e.g., target cells). For example, the counter electrode can be positioned on the bottom of a culture plate or other substrate. The tip-electrodes and a single, or plurality of counter electrodes, may be coupled to a single or several current- or voltage generators for delivery of electric field(s). One or a few counter electrodes may be provided for electroporation of several spots or locations, e.g., in one confluent cell culture. In this aspect, the counter electrode can be positioned in the bottom of a target container which contains multiple nontarget elements (e.g., nontarget cells) along with one or more target elements (e.g., target cells). For example, the counter electrode can be positioned on the bottom of a culture plate or other substrate. The tip-electrodes and a single, or plurality of counter electrodes, may be coupled to a single or several current- or voltage generators for delivery of electric field(s).

FIGS. 3A-C show an example of an embodiment where tip-electrodes are arranged in parallel in one plate. The plate consists of three different layers where (1) contain wells that act both as electrodes and electrolyte reservoirs and are made at least in part in a conducting material, (2) is a non-conducting layer with parallel tips corresponding to the wells in (1), and (3) is a counter electrode layer, here illustrated with individual circular counter electrodes for each tip-electrode. FIG. 3A is a close-up of one individual tip-electrode fabricated in this fashion and FIG. 3B illustrates a plate with a two-dimensional matrix of parallel tip-electrodes. The number of layers and design of electrodes can vary, depending on whether a large or small electrode area is most suitable. For example a filament can be molded or mounted into the plate, exposing the same electrode area in all tip-electrodes.

Additionally, a system of microfluidic channels can be provided on the upper most layer of the tip-electrode plate. Such channels can facilitate more advanced delivery applications, for example, delivery of plugs of agents, separated by buffer, or sequential delivery of several different agents, etc. Microfluidic applications will be discussed in further detail below.

Target Containers

As discussed above, the system of the invention preferably comprises a target container for containing one or more targets for exposure to electric fields and agent or conditions provided by tip-electrodes or tip-electrode plates. Although referred to as a "container" the target container does not necessarily comprise walls but may be a substantially planar substrate, such as a glass slide, microfluidic chip, or membrane, provided that targets are relatively localized, e.g., stably associated with a location on the substrate for a time sufficient to be targeted and exposed to an electric field and/or delivery of an agent. In one aspect, a target is surrounded by a plurality of non-target elements, e.g., the target is one or more cells in a population of cells in suspension, adhered to the bottom of a culture dish, or in a tissue slice or tissue explant. Cells may be from primary or established cell cultures, or from dissected tissue. In one aspect, the target container comprises a microtiter plate.

Example of plates of varying size and varying number of wells are shown in FIGS. 7A-D. The Figures exemplify different plates for culturing cells before and/or after electroporation depending on whether a single spot (FIG. 7A) or several spots (FIGS. 7B-D) are to be electroporated and if individual wells (FIGS. 7B and C) or large confluent cultures (FIG. 7D) are used.

Preferably plates fitting in commercially available automated workstations, such as robotic pipetting stations or plate readers, are used. Cells can be grown as confluent cultures or in designed patterns defined by surface chemistry or surface topography of a cell plate or both. For optimal read-out of electroporation experiments, a cell culturing plate is preferably made from an optically transmissive material. It is also possible to design cell-culturing plates with integrated microfluidic channels, for more advanced liquid delivery, for example, for rinsing or superfusion of electroporated cells with buffer or for supplying drugs to the cells in a controlled fashion. Microfluidic solutions will be discussed in further details below.

Microfluidic Channels

Several parts of the targeting/delivery system may include microfluidic channels for liquid solution delivery, for example, the cell-culturing plate, the electrode plate, if removable tip-electrodes are employed, or the tip-electrode plate. Networks of conducting electrodes and microfluidic channels for delivery and/or distribution of liquids can be patterned and directed to any chosen number of tip-electrodes mounted or fabricated as part of an electrode plate. Additionally or alternatively, microfluidic channels may be integrated in the target container/cell culturing plate. This is schematically illustrated in FIG. 11A-C.

Figure 11:
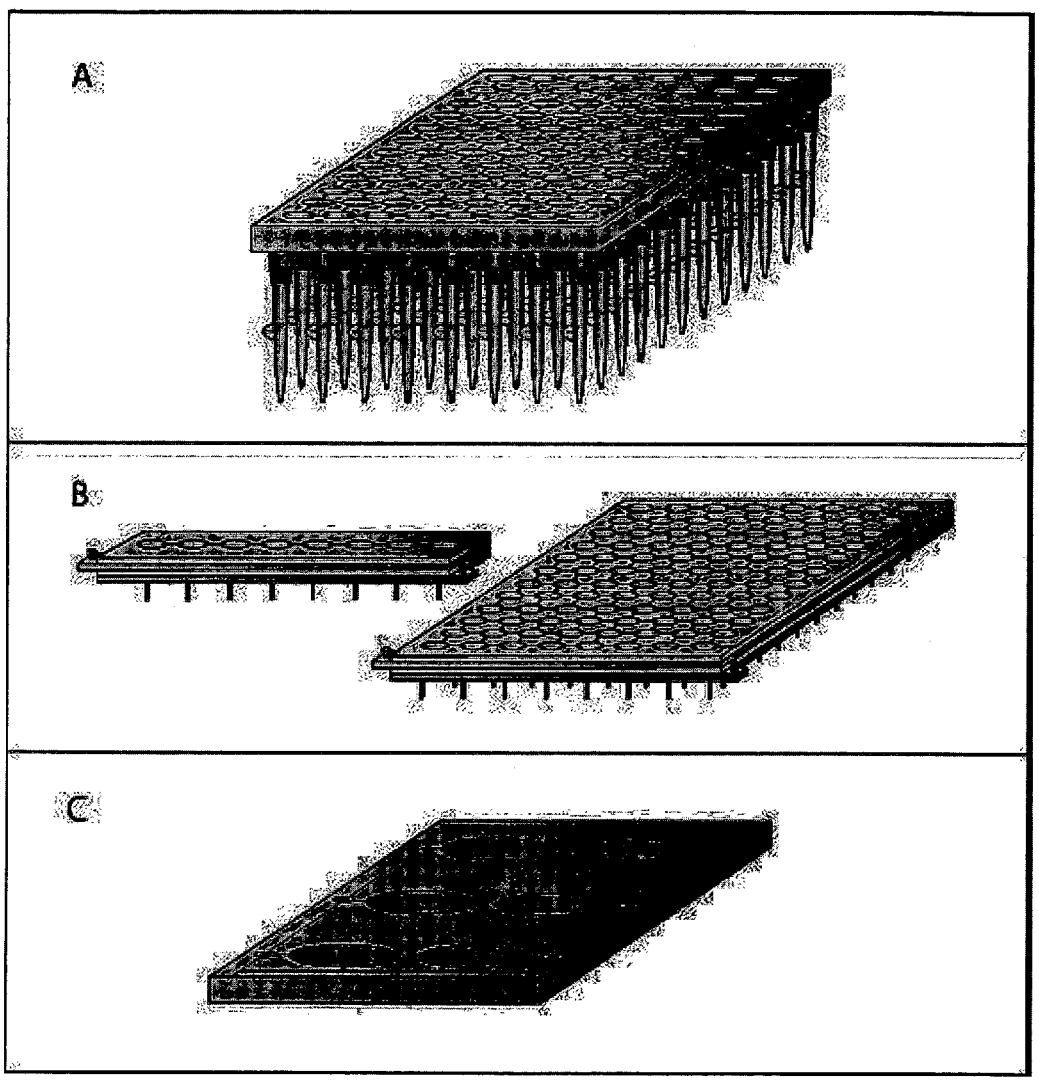
FIG. 11A-C illustrate how microfluidic channels can be integrated in different parts of an electroporation system of the invention for distribution and exchange of liquid solutions. For example, microfluidic channels can be integrated in the tip-electrode plate (FIG. 11A) or in the electrode plate (FIG. 11B) for administration of plugs of agents, or for sequential delivery of one or several agents through the tip-electrodes. Microfluidic channels can also be integrated in the cell-culturing plate as shown (FIG. 11C) for rapid exchange of the cell-surrounding solution, or for continuous rinsing/perfusion of the solution in the cell culture.

For example, microfluidic channels can be integrated in the tip-electrode plate, as shown in FIG. 11A or in the electrode plate as shown in FIG. 11B, for administration of plugs of agents, or sequential delivery of one or several agents through the tip-electrodes. Microfluidic channels can also be integrated in a cell-culturing plate as shown in FIG. 11C for rapid exchange of a cell-surrounding solution, or continuous rinsing/perfusion of the solution in a cell culture.

Microfluidic delivery of solution to a target-containing solution, such as a cell bath, or a solution reservoir in a tip-electrode-plate or electrode plate can be provided by fabricating one or more microchannels in the substrate whose outlets intersects with or feeds into the respective part of the target container containing the solution ("target reservoir") or reservoir in the electrode plate ("electrode plate reservoir"), (collectively, "reservoirs"). The substrate can be configured as a two-dimensional structure, as described further below. The substrate generally comprises a plurality of microchannels whose outlets intersect with one or several of the reservoirs.

In one aspect, each microchannel comprises at least one inlet (e.g., for receiving a sample or a buffer). Preferably, the inlets receive solution from containers that conform in geometry and placement on the substrate to the geometry and placement of wells in an industry-standard microtiter plate. Microchannels can be fabricated using methods routine in the art, such as deep reactive ion etching, soft lithography, etc. Channel width can vary depending upon the application, as described further below, and generally ranges from about 0.1 µm to about 10 mm, preferably, from about 1 µm to about 150 µm, while the dimensions of the reservoirs may vary depending on the arrangement of channel outlets feeding into the reservoirs.

Preferably, solutions contained in the microchannels and the reservoirs can be rapidly and efficiently replaced and exchanged. Rapid solution exchange can be achieved using a variety of different microchannel network geometries. In one aspect, a plurality of microchannels converge or feed into the reservoir, while in another aspect, a plurality of microchannels converge into a single channel which itself converges into a reservoir. The plurality of microchannels can comprise interdigitating channels for substance and buffer delivery, respectively.

The microchannels can be used to deliver and withdraw reagents, drugs, cell-inernalizing agents, etc, from cells. Delivery to and withdrawal from reservoirs can be made extremely fast, e.g., sub-microseconds, if appropriately designed. Additionally, a microfluidic network can be deigned in a particular manner to create gradients of substances in the microchannels of the substrate (see, e.g., Chiu et al., JACS). Exemplary constructions are described below.

Planar Radial Spokes-Wheel Format

In this construction, a large number (e.g., 96-1024) of microchannels are arranged as radial spokes which converge into a reservoir with dimensions ranging from about 10 µm to about 10 mm. The number of microchannels used is selected to accommodate the number of sample wells in an industry-standard microtiter plate, e.g., 96 to 1024 wells. In addition to the number of microchannels that matches the number of inputs from the well plates, there are preferably, at least two additional microchannels, one for the delivery of buffer and the other for waste removal.

In order to provide for efficient replacement of fluids contained in the reservoir by incoming fluids from the channels, the angle between the input channel and waste channel is optimized. Fluid mixing and replacement is optimal when this angle is about 180° and gets progressively worse as this angle decreases towards 0 degrees. For high flow rates (cm/s to m/s), the effect of this angle becomes progressively more important, while for low flow rates, the angle between the input channel and waste channel is less important.

To maximize efficient replacement of fluids at high flow rates, the number of radial channels can be increased such that each input channel will have a corresponding waste channel, rather than having all input channels share a common waste channel. In this format, all angles between input and output channels are about 180 degrees, ensuring optimal fluid replacement. Another strategy involves the use of branched channel geometries, as described further below.

Branched Channel Format

In this design, preferably only two channels are directed into the reservoir, one for the delivery of compounds and the other for waste. Rather than separating all the input channels and converging the outlets of each input channel so they feed into the reservoir, channels are arranged in a branched geometry. To interface with 96-1024 well plates, the single delivery channel is connected to a multitude of input microchannels, each input channels receiving input from a different well of a 96-1024 well plate. The delivery of the large number of compounds into the reservoir in rapid succession is achieved by the controlled and multiplexed delivery of fluids containing compounds into the single channel feeding directly into the reservoir.

In one preferred embodiment of this design, a "fish-bone" structure is fabricated with each "bone" corresponding to a substance delivery microchannel which intersects with a main "spine" microchannel which is connected to a buffer container. The rapid and sequential delivery of substance and buffer into the reservoir is achieved by first applying a positive pressure to one of the substance delivery microchannels, thus introducing a plug of sample from that microchannel into the main microchannel containing the buffer. This plug is introduced into the reservoir by applying positive pressure to the buffer container, which carries the plug into the reservoir, and then washes with the buffer solution. This cycle of delivery of sample and buffer is repeated with different samples contained in different microchannels. The dimensions (width and thickness) of the microchannel (for both sample delivery and buffer delivery) can be highly variable, with typical dimensions ranging from about 1-100 µm, and preferably from about 10-90 µm. Flow rate also may be varied with preferred flow rates ranging from µm/s to cm/s.

Pressure is isotropic, therefore, upon application of a positive or negative pressure, fluids will flow along any pressure drop without preference to any particular direction. Therefore, preferably, passive one-way valves are integrated at the junction between substance delivery microchannels and the main buffer channel. The purpose of these integrated one-way valves is to prevent any flow from the main buffer channel into each of the substance delivery microchannels upon application of a positive pressure to the buffer container, while allowing flow from each of the substance delivery microchannels into the main buffer channels when positive pressure is applied to containers providing sample to these microchannels. There are numerous suitable designs for microfluidic valves as well as pumping mechanisms.

Although the discussion below emphasizes pressure driven flow owing to its simplicity of implementation, a number of appropriate means can be designed for transporting liquids in microchannels, including but not limited to, pressure-driven flow, electro-osmotic flow, surface-tension driven flow, moving-wall driven flow, thermo-gradient driven flow, ultrasound-induced flow, and shear-driven flow. These techniques are known in the art.

Valving and Pumping

Using Septums To Address Individual Microchannels

In this scheme, containers that connect to each of the microchannels for providing sources of agents are sealed by a septum. Because the septum forms an airtight seal, application of a positive pressure (e.g., with air or nitrogen) via a needle or a tube inserted through the septum will cause fluid to flow down the microchannel into the reservoir (e.g., to the center of a spokes-wheel where radial microchannels converge). Application of a negative pressure with a small suction through the needle or tubing inserted through the septum will cause fluid to be withdrawn in the opposite direction.

An array of such needle-septum arrangements allows each container to be individually addressed, and therefore, each microchannel. The use of this scheme permits the simultaneous and sequential pumping and valving of the fluids contained within each of the microchannels. By exercising precise control over positive and negative pressure applied to each of the microchannels, controlled fluid flow and compound delivery into each reservoir can be achieved. For designs that do not require individual addressing of the microchannels, a single or a few septa with a single or a few pressure control devices will suffice.

Controlling Fluidic Resistance by Varying Channel Dimensions

Although the above design using individual septa offers great flexibility and control, for certain applications in which the sequence of compound delivery and fluid flow is predetermined, a simpler design offers simplicity and ease of implementation. In this scheme, equal positive pressure is applied to all containers, for example, by using pressurized air applied homogeneously to all containers via a single septum, or through the use of gravity flow caused by the difference in height between inlet and outlet reservoirs. The rapid sequential delivery of compounds from each microchannel into the reservoir is accomplished by varying the fluidic resistance of each microchannel, which is easily achieved by varying the width and length of the each microchannel.

Fluidic resistance increases linearly with length and to the fourth power of the diameter for a circular capillary. By gradually and systematically varying the dimension of each microchannel, the time delay among the microchannels in their delivery of compounds onto one or more sensors in a sensor chamber can be controlled.

Control of Fluid Flow with External Valves

In this configuration, compounds from each of the wells of an array well plate are introduced through external tubings or capillaries which are connected to corresponding microchannels. External valves attached to these external tubings or capillaries can be used to control fluid flow. A number of suitable external valves exist, including ones actuated manually, mechanically, electronically, pneumatically, magnetically, fluidically, or by chemical means (e.g., hydrogels).

Control of Fluid Flow with Internal Valves

Rather than controlling fluid flow with external valves, there are also a number of chip-based valves that can be used. These chip-based valves can be based on some of the same principles used for the external valves, or can be completely different, such as ball valves, bubble valves, electrokinetic valves, diaphragm valves, and one-shot valves. The advantage of using chip-based valves is that they are inherently suited for integration with microfluidic systems. Of particular relevance are passive one-way valves, which are preferred for implementing some of the designs mentioned in above (e.g., such as the branched channel format).

Electroporation Systems

In one aspect, a targeting and delivery system for selectively exposing targets to an electric field and delivering one or more agents is adapted for electroporation of cells and/or intracellular organelles and/or membrane fractions. The system provides highly spatially resolved electric fields to physically break the membrane barrier of membrane-enclosed structures as a means to provide a diffusion pathway for agents to enter such membrane-enclosed structures and hence to alter the biochemical content of, for example, single cells and organelles.

In one aspect, such highly focused electric fields are obtained by using at least one tip-electrode with an outer diameter in the range of a few nanometres to a few micrometers. This enables electroporation of single cells and even intracellular structures. Also, this method allows for the controlled disposition of small amounts of agents to well-defined loci such as single macromolecules on a surface. The tip-electrode is controlled individually with a high-graduation micropositioner, thereby enabling precise electrode alignment with respect to a structure to be permeabilised. During the effective pore-open time, cell-impermeant solutes added to the extracellular or extraorganellar medium can enter the cell or organelle interior by diffusion.

In another aspect, an electroporation system comprising at least two tip electrodes are provided. Because of the highly focused electric fields produced by the two electrodes, extremely short inter-electrode distances may be used, permitting electroporation of, and agent delivery into targets that are within nanometers-to-micrometers apart. Of course targets placed at larger separation distances up to, for example, millimeters or centimeters, apart are also possible. For example, the system permits electroporate in a parallel fashion of multiple targets. The parameters of the electric fields and agent delivery may be independently controlled for each tip electrode. In one aspect, the tip electrodes are movable in three dimensional space, while in another aspect, the at least two tip electrodes are fixed with respect to movement in an x- and y-direction with respect to each other.

FIG. 1 is a schematic diagram showing a system for electroporation using tip-electrodes of one aspect of the invention. The system comprises an electrolyte-filled tip-electrode (1) having a solid electrically conducting material or surface (2) in electrical contact with an electrode plate (3). The electrode plate is connected to a pulse generator (4) for delivery of voltage or current pulses through the tip-electrode and ground to the counter electrode (5). The tip-electrode is positioned in a cell bath (6) so the solution contained in the tip is in contact with the solution in the cell bath. The solution contained in the tip-electrode is a suitable conductive medium supplemented with the one or several agents of interest to be introduced into the cells. Preferably, the cell bath contains the same solution without the agents or a similar appropriate medium.

In the example shown in the FIG. 1, the tip-electrode comprises a pipette tip with an internalized platinum wire electrode that is in contact with a conducting ring plate on the outside of the tip-electrode. The conducting ring plate is brought in contact with a conducting layer in the electrode plate. The electrode plate contains four layers. An insulating layer with small areas exposing the second, conductive layer to enable contact to the tip-electrodes. The third layer is insulating to separate the electric pulse from the counter, e.g., ground, and the fourth is a conductive layer with internalized counter, e.g., ground electrodes which make contact with the cell bath. The design of the tip-electrode can be altered in a number of ways, as discussed above, as can the design of the counter electrode.

Fluid containing one or more cell-loading agents may be delivered to cells or cellular structures by some mode of pumping. For example, pressure-based pumping, pumping based on gravitational flow, electroosmosis, electrophoresis, or combinations thereof, may be used. Various macroscale devices can be interfaced to the electrode plate for agent and solution delivery to each tip-electrode.

The setup can be manufactured as separate parts or modules with the tip-electrodes being detachable from the electrode plate, or as an integrated system with the tips fixed in the electrode plate. Liquid handling and solution flow functions may be integrated in the system by including microfluidics in a combined tip and electrode plate and/or in the cell plate. For example, microfluidic channels, as discussed above, may be provided for supplying drugs, dyes, genes, buffers, etc. to the cells before, during or after the electroporation treatment, or alternatively a more traditional micro-dispensing technology can be utilized.

Preferably, the system further comprises a system processor for controlling one or more of: the operation of the pulse generator, fluid and agent delivery to the tip-electrode plates and/or to microfluidic channels where such are included, operation of valves and switches present for directing fluid flow through the microchannels; movement of system components (e.g., scanning by tip-electrodes, tip-electrode plates, counter electrodes (where these are independently movable), cell plates, and the like), operation and data analysis by a detector, and the like. Preferably, the system also comprises a user device in communication with the system processor which comprises a graphical interface for displaying operations of the system and for altering system parameters.

For example, many different schemes may be envisioned in which the pulse generator is programmed or manually controlled to provide for optimal loading conditions for different types of cell-loading agents and cells. Thus, both pulse duration, polarity, waveform, pulse amplitude, and other pertinent parameters may be changed during the course of cell-loading using a tip-electrode. Preferably, a programmable pulse generator is used for controlling such parameters.

In one aspect, a complete system for performing electroporation consists of the targeting/delivery device (with tip-electrodes, electrode plate and a cell culture plate), coupled to an electric field generator and liquid pumping device controlled by a computer software, and combined with a suitable readout system for detection of the electroporation treatment and collection and analysis of data. This is exemplified in FIG. 12.

Figure 7:
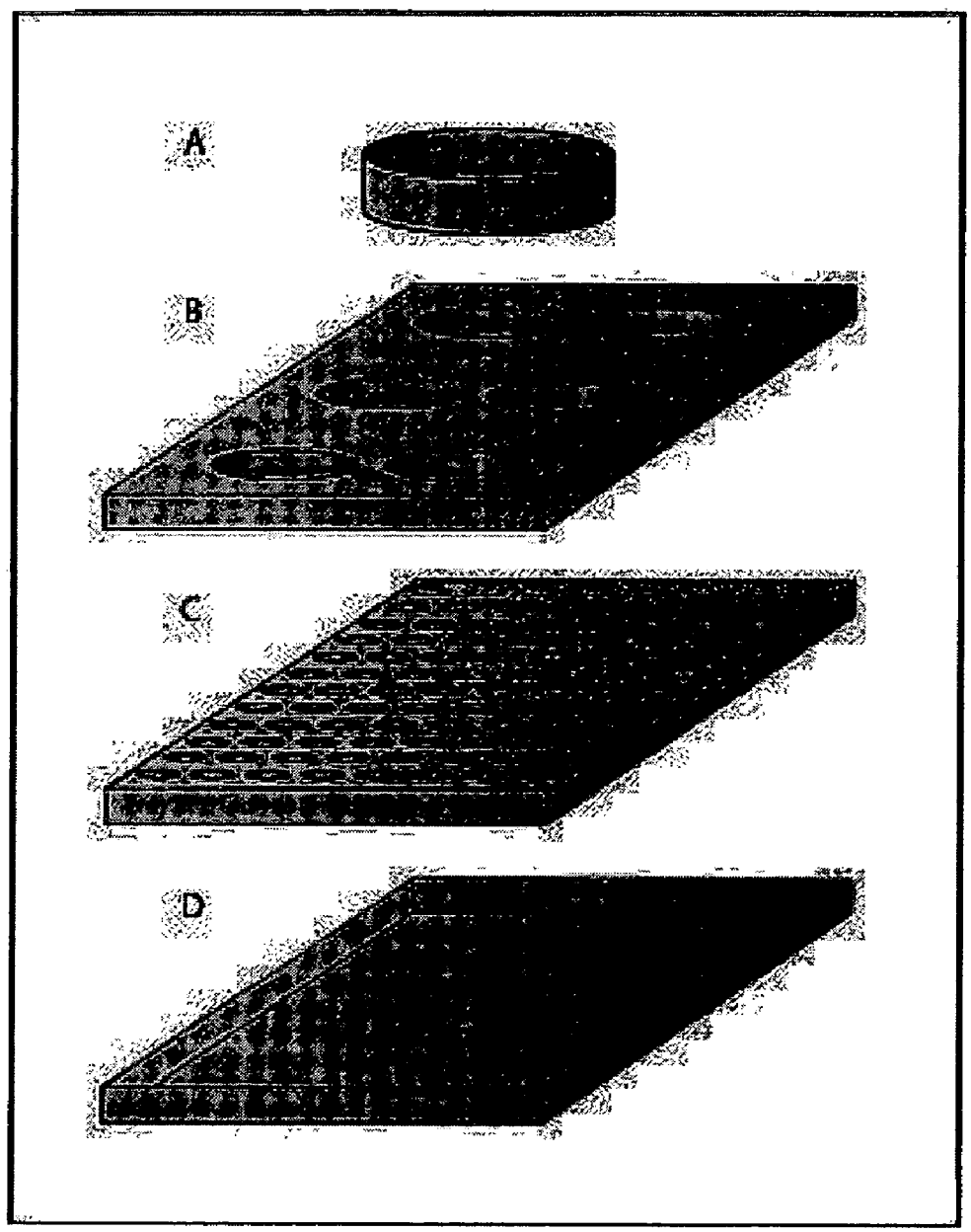
FIGS. 7A-D exemplifies different cell containers or plates for culturing cells of different aspects of the invention.

In another aspect of the invention, the electroporation system is modular and one or more of the system components are removable from the system and interchangeable with other components. For example, an electroplate for receiving a single tip may be replaced by an electrode plate for receiving multiple tip-electrodes. Similarly, the system may include a variety of interchangeable cell plates as shown in FIG. 7 for example. Alternatively, or additionally certain combinations of components may be integrated, e.g., the tip-electrodes may be integral parts of an electrode plate and not removable from the electrode plate.

Figure 8:
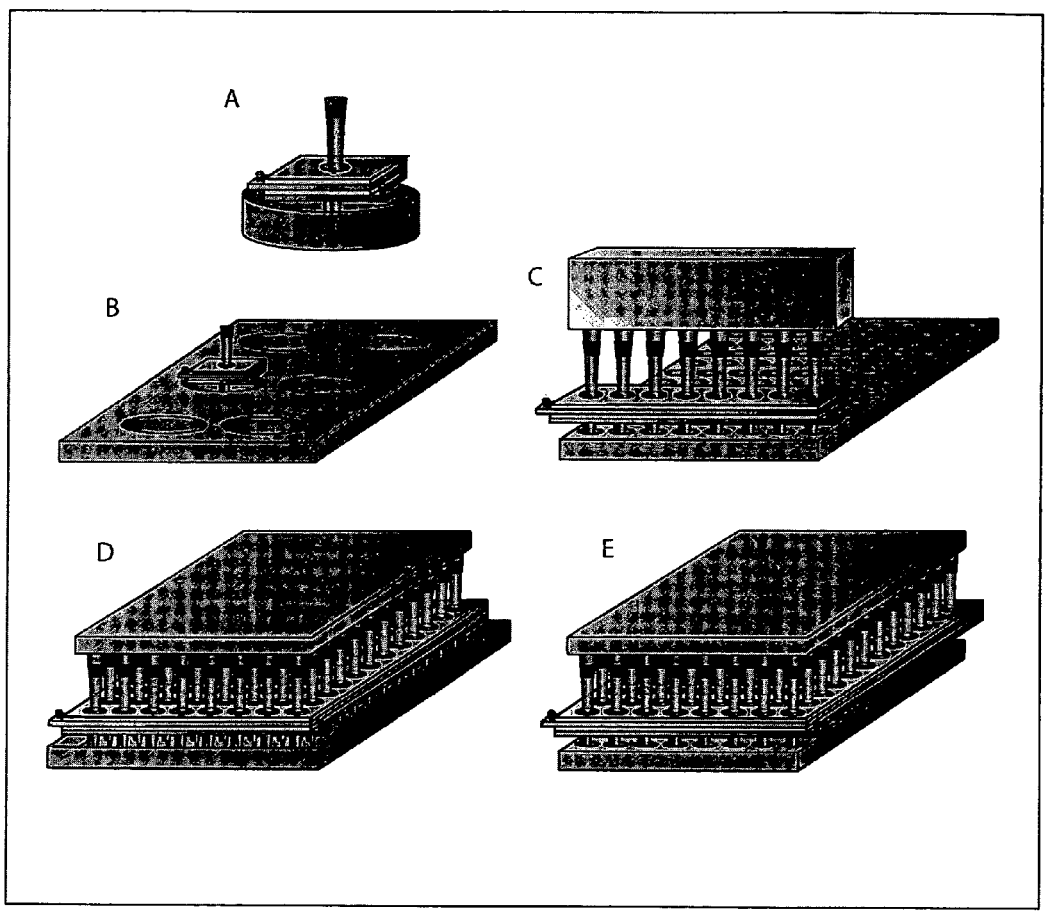
FIGS. 8A-E illustrate different electroporation systems of the invention with varying numbers of tip-electrodes and wells in cell containers, such as microtiter plates.

FIG. 8 illustrates different combinations of tips, tip plates and cell containers of the present invention.

Figure 12:
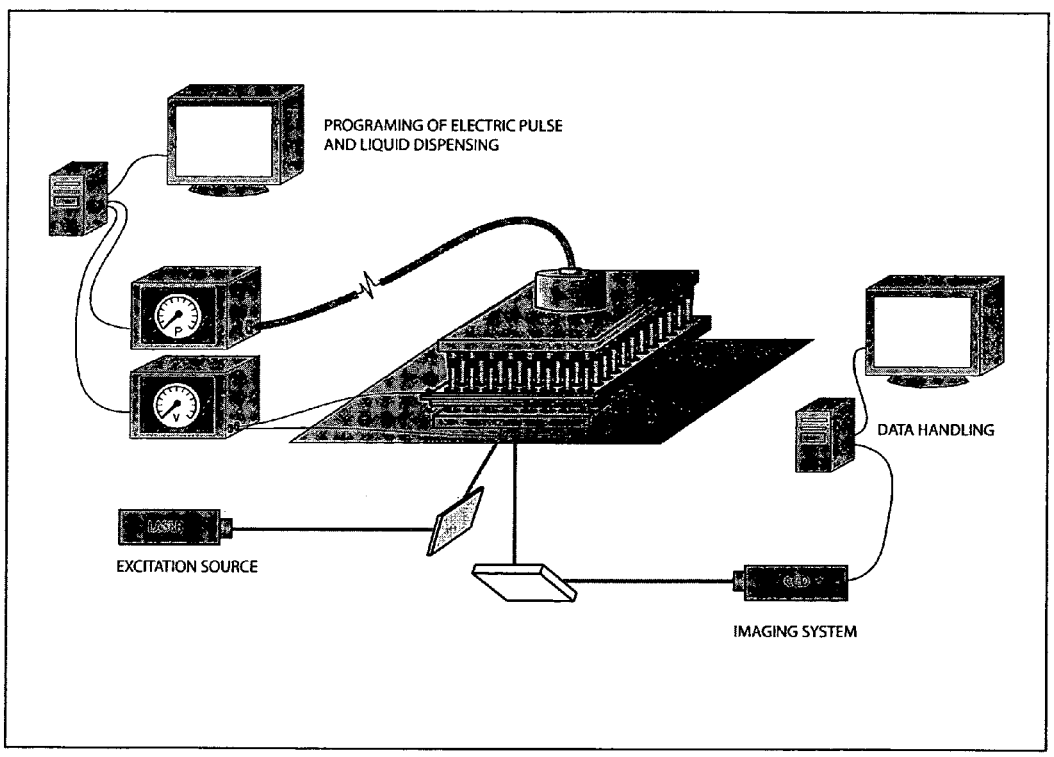
FIG. 12 shows an electroporation system of one aspect of the invention, in addition to a tip-electrode plate and cell plate, a pulse generator, liquid dispensing system, and a detector.

FIG. 12 shows the electroporation setup in combination with additional equipment. A pulse generator and liquid dispensing system is preferably controlled by a software program, for precise calibration of electric field parameters, number of pulses, pulse length and amount of solution to be dispended. In the example illustrated by the Figure, a detector is provided to detect electroporation and/or introduction of an agent into a cell. In one aspect, the detector is capable of detecting fluorescently labeled molecules. For example, the detector may comprise a laser for providing an excitation source, a CCD camera and computer for collecting and analyzing data. The electroporation systems of the invention are easily mounted on microscopy platforms, or can be manufactured as an integrated part of a robotic pipetting station and/or plate reader system.

Operation of an Electroporation System

Positioning

The tip-electrodes need to be positioned in proximity to target(s) to be electroporated. Movement of the tip-electrode in the z-direction can be controlled by using automatically or robotically controlled micropositioners, or by using any physical hinder, such as vertical or horizontal guiding objects for forcing the device into a defined position. In certain embodiments, the tip electrode may be rotated. If a non-confluent culture is targeted, the tip-electrode also needs to be positioned in x-, y-direction relative to the target. This can also be achieved by a conventional micropositioning-technique, but rather than moving the device while keeping the cell culture fixed, it is possible to use motorized translation stages or other similar devices for moving the cell culture while keeping the tip-electrodes at a fixed position.

In one aspect, a simple mechanical solution is used to simultaneously position multiple tip-electrodes over multiple targets. The electrode plate may be configured with a suitable number of mounting points for tip-electrodes. For example, the plate may comprise 96 mounting points corresponding to the center-to-center distance between an industry standard 96-well microtiter plate. Each mount point preferably contains a hole through the plate and a part suitable for attaching the pipette.

Positioning may be effected by pushing the electrode plate comprising the tip-electrodes downwards by equipping the electrode plate with positioning mechanisms. As used herein, a "positioning mechanism" comprises a part, or mechanism which serves to keep an exact distance between the tip-electrode and a target container such as a cell plate. Positioning mechanisms, preferably, one for each tip-electrode, cause each tip-electrode to individually stop at a predefined distance from each surface.

Figure 13:
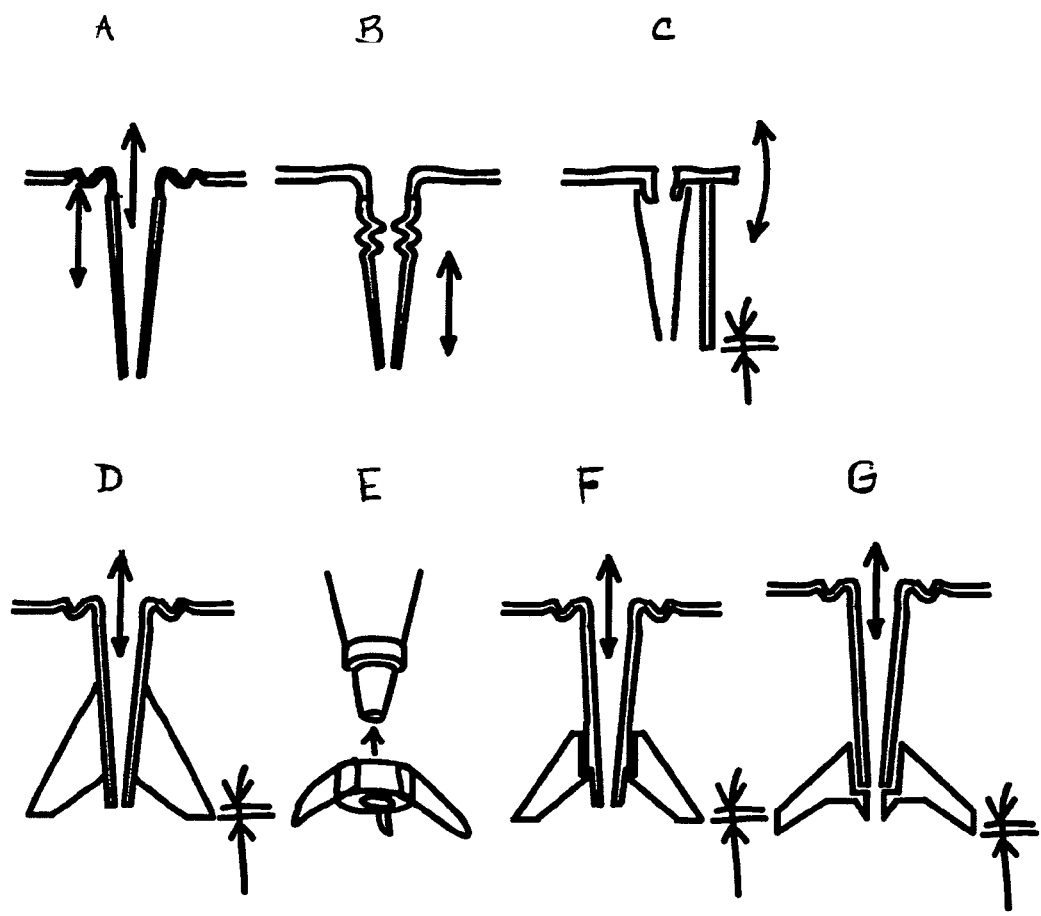
FIGS. 13A-G show different positioning mechanisms for controlling the distance between the target-facing end of the electrode and a target.

In one aspect, a flexible mount is provided which allows a restricted vertical mobility for a tip-electrode. Suspension flexibility can be achieved in a number of non-limiting ways. For example, as shown in FIG. 13A, the part closest to the mount point in the electrode plate may comprise a spring or a section with "bellow like" concentric circular "circles" which in combination with the properties of the material create a spring effect allowing the mount point to move. In another aspect, as shown in FIG. 13B, the housing of the tip-electrode can include a flexible bellows that provides flexibility In the example shown in the Figure, the mount point is fixed to the plate. In a further aspect, as shown in FIG. 13C, a horizontal flexible bar is provided which comprises a mount point at one end fixed to the electrode plate, permitting the mount point to move.

A positioning mechanism may be provided which is fixed in its movement relative to a tip-electrode. The positioning mechanism comprises a surface which limits tip-electrode movement to a pre-definable distance from the surface. However, preferably, the surface is configured to minimize contact between the tip and the surface. In one aspect, the positioning mechanism comprises a vertical bar as shown in FIG. 13C which is attached to a moving mount point. The lower tip of the bar impedes further movement of the tip-electrode when it contacts the surface of the positioning mechanism. In another aspect, shown in FIGS. 13E, F, and G, the positioning mechanism is mounted to the tip or is an integral part of the tip-electrode as shown in FIG. 13D.

In the embodiment shown in the Figures, the mechanism has two or more "wings" which can end in small points and a lumen designed to fit at least a portion of the tip-electrode. The tip-electrode and positioning mechanism may be designed either to permit the tip-electrode to come very close to target (FIG. 1 3F) before its further motion is blocked or prevented from further passage through the lumen of the positioning mechanism (FIG. 13G). In the latter case, the distance of the tip-electrode from the surface is dependent on the geometry of the positioning device only. In the example, shown in FIG. 13G, a portion of the positioning mechanism itself may be tapered to a tip which acts as the target-facing end and acts to additionally focus agent delivery and/or the electric field.

In a further aspect, one or more of the tip-electrode(s), electrode plate, cell container/cell plate is moveable in an x-, -y, and/or z-direction. For example, a single tip-electrode or plurality of tip-electrodes in an electrode plate may be scanned relative to a target in a cell plate by moving the tip-electrode, tip-electrode plate and/or cell plate to effect sequential exposure to an electric field and/different agents and/or electrolyte buffer.

Controlling the Electric Field

The magnitude and distribution of electrical fields needed to cause electroporation vary largely depending on the type and the size of the treated cell structure. It is also possible to vary the potential, polarity, and waveform over the tip-electrode during the time course of agent delivery to a cell structure, i.e., delivery and electroporation is not performed at a constant electric field strength. Programming of electrical field parameters by a system processor in communication with a power supply, such as a pulse generator, is particularly preferred when several compounds are introduced to a cell structure in a sequential manner.

The duration of a pulse may vary from a few microseconds to several minutes, depending on the type and the size of the treated cell structure as well as depending on the nature of the cell-loading agent. The pulse generator transmits voltage or current pulses through the tip-electrodes of sufficient strength to transiently alter dielectric properties of membranes, thereby creating pores in the membranes suitable for the introduction of otherwise membrane impermeant molecules.

Preferably, the pulse generator generates an electric pulse or a pulse train, either as voltage or as current, that gives rise to an electric field strength that is from about 0.1 kV/cm to 10 kV/cm at the surface of the cell structures to be electroporated, and more preferably it is from about 0.5 kV/cm to 1.5 kV/cm at these surfaces. The electric field can be delivered as a single pulse, or as a pulse train of several pulses. Preferably a pulse is from about 0.1 µs to several minutes, e.g., about 1-10 minutes. More preferably a pulse ranges from about 1 µs to 5 s, and most preferably it is less than 100 ms. The number of pulses is preferably between about 1 and about 1000, and more preferably between about 1 and about 50. When more than one pulse is used, the interval between the pulses is preferably from about 0.1 µs to several minutes, and more preferably between about 1 µs and 5 s.

During application of the electric field pulse, the cell structure is permeabilized through pore formation, allowing polar and charged solutes present in the extracellular medium and that otherwise cannot pass through the biological bilayer membranes, to enter the interior of the cell structure through diffusion or hydrodynamic flow. The spatial resolution afforded by the system of the invention is dictated by, for example, the inner and outer diameter of the tip-electrode, the applied electric field strength and the gap distance between the tip-electrode and the electroporation target. This gap distance depends mainly on the size of the cellular structure to be electroporated and may thus vary between a few nanometers to several hundred micrometers. Depending on the composition of the buffer, the conditions are changed at the electrodes. Electrochemical reactions at the electrodes, e.g., reduction of water and oxidation of chloride, cause some loss in voltage and the effective voltage can be calculated for every given set of electrode materials and buffer systems to achieve optimal electroporation as is known in the art.

When using electrically insulating tips, the electric field needed for electroporation of a cell structure is carried by the electrolytes contained in the solution in the lumen of the tip-electrodes. Where the electrode component of the tip-electrode is an electrically conducting surface provided in the form of a rod, cylinder or wire inserted into the lumen, the surface feeds current or voltage supplied by a pulse generator into the electrolyte solution. As discussed above, the positioning of such a surface electrodes are not limited to the back-end of the tip-electrode, the rod/wire/cylinder, etc., can be placed anywhere on the inside of the tip-electrode. When the conducting surface is a coating of conducting material on at least a portion of the walls of the housing (e.g., the walls defining the lumen), current or voltage supplied from the pulse generator is transported to the coating and further into the electrolyte solution either via electrodes inserted through walls of the housing of the tip-electrode or through the receiving end of the housing, or through a continuity in the coating which faces the outside of the tip-electrode which is in communication with the pulse generator.

Agent Delivery

Figure 10:
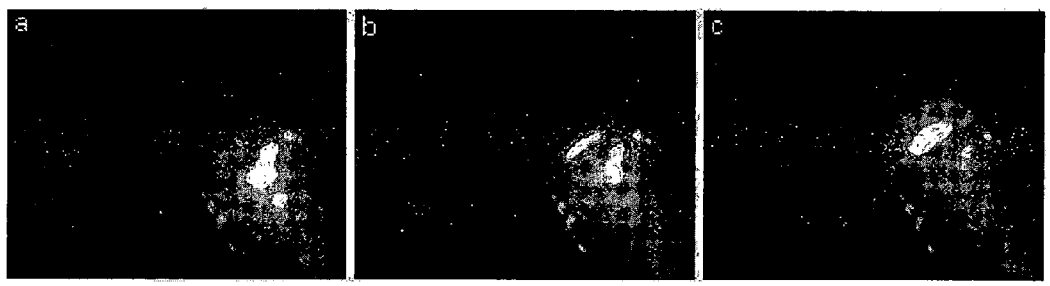
FIGS. 10A-C show ejection of solution from a tip-electrode caused by electrophoresis and electroosmosis during a 50 ms pulse application. The tip-electrode contained 100 μm fluorescein in pH 9 buffer, at 0 ms (FIG. 10A), 25 ms (FIG. 10B), and 50 ms (FIG. 10C). The bulk solution in which the tip is bathed is buffered at pH 4 to quench fluorescence. The flow results from electroosmotic/electrophoretic migration of fluorescein in the electric field; no additional pressure is applied.

As discussed above, fluid containing one or more cell-loading agents may be delivered to cells or cellular structures by a number of means including, but not limited to, pressure-based pumping, gravitational flow, electroosmosis, electrophoresis, or combinations thereof. Generation of an electroosmotic flow requires a tip-electrode with an appropriate inner diameter and length, and also, that the inner surface area of the tip-electrode be electrically charged. A flow profile created outside a tip-electrode of 500 µm inner diameter during a pulse is illustrated in FIG. 10, for example.

When electroosmosis or electrophoresis is not used for pumping, any appropriate apparatus for creating the flow such as a peristaltic pump, a microinjector/micropump, or other device for driving fluids may be connected to the inlet/receiving end of the tip-electrodes before, during, or after electroporation.

In some aspects, it may sometimes be advantageous to deliver agents to cells using a pumping method and to apply electric pulses for electroporation at periodic intervals. For example, pumping may be synchronized with application of electric fields, such that a volume of electrolyte contained in the lumen of a tip-electrode in a tip-electrode is pumped to a cell surface, and after a selected time interval, voltage suitable for electroporation is applied through the electrically conducting surface of the tip-electrode. The voltage may be turned off and a new volume of solution/agent may be delivered. Peristaltic, syringe, or other suitable pumps may be used to provide pulsed delivery of solution/agent while voltage or current pulses are provided by a pulse generator in communication with the electrode tip(s).

Depending on the charge of the agent to be internalized into the cells, (which is often pH dependent), it is preferable to use a pulse of a polarity that will force the flow of the electrolyte solution out towards the target and not attract the flow of solution in the cell container back into the tip-electrode. However, pressure may be applied, as discussed above, in order to direct the flow of agents contained in the tip-electrode to the cell-containing solution, e.g., when the electric pulse is not efficient for delivery through electromigration.

FIGS. 10A-C show ejection of solution from the tip-electrode by electrophoresis and electroosmosis during a 50 ms pulse application. The tip-electrode contained 100 µm fluorescein in a electrolyte buffered at pH 9. FIG. 10A shows ejection at 0 ms. FIG. 10B shows ejection at 25 ms. FIG. 10C shows ejection at 50 ms. The bulk solution was buffered at pH 4 to quench fluorescence. The flow is a result of the electroosmotic/electrophoretic migration of fluorescein in the electric field; no additional pressure is applied.

After electroporation of the target, washing of-the cell plate can be performed in order to remove excess agent(s) if needed. The buffer is then replaced by a agent-deficient buffer ("washing buffer") that in turn can be replaced with an incubation buffer such as a cell culture growth media or any other media of choice. In one aspect, washing buffer may be delivered through the same tip electrode that delivered agent, using a fluid delivery system comprising both buffer and agent lines feeding into the tip electrode, using appropriate valves or switching mechanisms whose operation is preferably under programmable control by a system processor. Alternatively, different solutions can be aspirated into the apical end of the electrode tips or back-filled into electrode tips or provided by fluidic channels as described above.

Methods of Treatment

The tip-electrodes and electrode systems of the invention offer high spatial control allowing treatment of targets with different agents and different pulse protocols despite small separation distances between the targets.

In particular, the invention enables rapid screening, identification, alteration, functional characterization, and detection of intracellular targets based on permeabilization of phospholipid bilayer membranes, i.e., electroporation. The method is scalable and a single solitary cell, a plurality of cells, or a large population of several million cells can be targeted. Thus, systems of the invention permit rapid screening of drugs, identification and validation of intracellular drug targets and screening of drug-like substances that affect intracellular chemistry, in an automated and parallel manner.

Agents

Using systems of the invention, it is possible to introduce essentially any kind of substance, agent or cell-loading agent into the electroporated cell structures. As used herein, a "cell-loading agent" refers to an agent that is typically polar and is typically unable to pass biological membranes spontaneously. Examples of such substances or cell-loading agents include, but are not limited to, the following agents: genes; gene analogs; RNA; RNA analogs; siRNA; antisense oligonucleotides; ribozymes; DNA; DNA analogs; aptamers; colloidal particles; nanoparticles; receptors; receptor ligands; receptor antagonists; receptor agonists; receptor blockers; enzymes; enzyme substrates; enzyme inhibitors; enzyme modulators, including allosteric enzyme modulators; proteins; protein analogs; polypeptides; polypeptide analogs; amino acids; amino acid analogs; peptides; peptide analogs; metabolites; metabolite analogs' oligonucleotides; oligonucleotide analogs; antigens; antigen analogs; haptens; hapten analogs; antibodies; antibody analogs; organelles; organelle analogs; cell nuclei; cell fractions; bacteria; viruses; viral particles; gametes; inorganic ions; organic ions; metal ions; metal clusters; agents that affects cellular chemistry; agents that affects cellular physics (e.g., motility of cells, mitosis, endocytosis, exocytosis, vacuole formation, function of actin, myosin, tubulin, and other structural proteins, etc.), agents that affect polymers (e.g., agents that affect DNA replication and protein translation, tubulin assembly, etc) as well as any combination of two or more of these agents.

As used herein, however, an "agent", also more generally refers to any property of a solution flowing through a tip-electrode that may be used to alter the solution environment around a target, for example, an agent introduced through the tip electrode may alter pH, temperature, ionic strength, osmolarity, viscosity and the like, of the solution environment around a target.

Targets

Exposure to an electric field and agent delivery from the tip-electrode is "spatially confined" in that it can be limited to a small spot corresponding to a target without exposing non-targets or while exposing other targets to different types of electric fields and agents by other tip-electrodes.

In one aspect, the tip-electrodes are used to facilitate delivery of agents to the cytoplasm of a small population of cells. These target cells may be in suspension with other cells ("non-target cells") or in a discrete location (i.e., a spatially confined location) on a surface or in a container in which the target cells may or may not be surrounded by other cells. For example, the target may be located in a well of a multiwell culture dish such as a microtiter plate or at spot on a surface stably associated with the surface through binding with one or matrix proteins, adhesion molecules, surface chemistry, physical topography, and the like.

The tip-electrodes may also be used to facilitate delivery to single cells and even intracellular compartments.

In one aspect, the tip-electrodes and systems of the invention are used for delivery of membrane-impermeant cell-loading agents to and/or into cell structures. It is preferred to target small numbers of cells (prokaryotic or eukaryotic) for electroporation, such as from about 1 to at least 100,000 000 cells, and more preferably from about 5-1,000 000 cells. These cells can be a part of, or all cells in a culture (suspended or adherent), a tissue slice, a tissue, or an organ, or cells patterned on a surface. Cellular structures that can be used may be intracellular structures, organelles (isolated or contained in living or dead cells), membranous vesicles, bacteria or a nanobacteria.

It is also possible to use the method of the present invention on cell structures formed of synthetic membrane structures such as liposomes or emulsion droplets. Such cell structure may be either one or several cells or one or several cellular structures. Additional cellular structures include, but are not limited to: mitochondria, smooth or rough endoplasmic reticulum, golgi apparatus, lysosomes, peroxisomes, nucleus, nucleolus, transport vesicles, synaptic vesicles, chloroplasts, and vacuoles.

Additional targets include molecules, macromolecules, and surfaces whose interactions with agents may be altered through exposure to a focused and tunable electric field. For example, targets can include, but are not limited to: nucleic acids, proteins, polypeptides, and peptides; enzymes; carbon fibers; chemical reactants; and the like and exposure to focused electric fields may facilitate hybridization, polymerization, catalysis, chemical synthesis, and other processes. In some aspects, sensitivity to electric field may be facilitated through labels (e.g., such as metal particles) that are coupled to such molecules. The focused electric fields can be used to orient molecules that are constant or inducible dipoles and to provide thermal excitation energy to reactants. As such, a system according to the invention may be used to control chemistry in confined regions and interfacial systems.

Electroporation In one aspect, the invention provides a method for delivery of primarily polar and hydrophilic substances contained in solution into the cytoplasm of a cell. Thus, the method provide means for breaking the cell membrane barrier by creating well-defined focused electric fields in the vicinity of the cells to be permeabilzed. The method can be applied to single or several cells, and be performed in a parallel manner to a plurality of single cells or a plurality of populations of cells, either on a homogeneous surface or isolated in a number of wells.

The method can also be used to deliver substances and electric fields on surfaces not containing cells for purposes of, e.g., patterning the surface with molecules or creating focused electric fields.

Single-cell electroporation may be performed using tip-electrodes of the invention by high resolution positioning of a tip electrode relative to a target cell in an adherent cell culture, tissue slice, tissue explant, array of cells stably associated with a substrate (e.g., through matrix molecules, adherent proteins, surface chemistry of the substrate, other cells, physical topography, etc.).

The method according to the invention can in principle be battery-operated because the spacing between the electrodes is small, typically 20 µm or less, which result in a high electric field strength with a small amplitude voltage pulse. This technique provides the first demonstration of selective solute-transfer into biological structures using highly focused electric fields of single-cell and subcellular dimensions.

Methods according to the invention can be used for biosensor applications where a cell or a cell-like structure is placed in a permebilising DC or AC electric field while supplemented with drugs or other compounds of interest. A special application is the combination of electroporation and miniaturised chemical separations, where hollow liquid electrodes made of fused silica or similar materials are used.

In one aspect, the method comprises providing at least one tip-electrode which is in communication with a power supply such as a pulse generator, providing at least one counter electrode, also connected to the power supply, placing the tip electrode in proximity to a cell structure, applying a highly focused electric field of a strength sufficient to obtain electroporation between the at least one tip-electrode and the at least one counter electrode.

In one aspect, tip electrode(s) and counter electrode(s) are independently controlled by high graduation micromanipulators. In another aspect, tip electrodes and counter electrodes move independently of each other only in the z-direction. In a further aspect, tip electrodes and counter electrodes are integral components of an electrode plate and do not move independently of each other.

In one aspect, the method comprises synchronizing electroporation with substance delivery through the tip-electrode.

The population of cells, cellular structures, single cell or single cellular structure may be pretreated before electroporation experiments. For example, a target may be loaded with a dye such as fluo-3-AM ester for detection of events that results in increased concentrations of calcium ions in the cytosol or it may be transfected with a labeled reporter gene or a gene encoding a fluorescent molecule (e.g., luciferase, GFP, EGFP, etc), half of a FRET pair, where production of signal requires successful electroporation and introduction of another molecule (e.g., an inducer of the reporter gene or the other half of a FRET pair). The cells may also be treated by other chemical or physical means in a cell container/cell plate. For example, drugs of interest may be added to the cell bathing solution before, during or, after the electroporation event. Delivery of such agents may be mediated through additional capillaries or pipettes added to the system, or via microfluidic channels integrated in the cell-culturing plate, either in bulk fashion (delivering to all cells or cell structures or to a majority of cells or cell structures) or locally (delivering only to the cells or cellular structures affected by the electric field).

The electric pulse from a pulse generator in communication with a tip-electrode may induce an electrophoretic and electroosmotic (depending on surface charge) flow of electrolyte contained in the tip-electrode. As the tip-electrode is filled with cell-loading agents, the flow delivers these agents at the site of pore formation. If a specific amount of agent is desired, or if delivery of agents to the cells is preferred before or after the electroporation pulse, external pressure may be provided to complement the electrophoretic flow for agent delivery to cell surface(s). The combination of pore formation, due to the electric pulse, and delivery of agents to the cell surfaces enables loading of materials into the cytoplasm or into organelles of cell(s).

Thus, the present invention provides a method for co-delivery of substances and a focused electric field to cells in a well-defined and spatially resolved manner.

The method may be used either for transferring solutes from an extracellular medium into a permeabilised cell structure, or for transferring solutes entrapped in the cell structure out to the extracellular medium. The method according to the invention may also be used for transferring a substance into or out from an organelle, even when the organelle is located inside a cell.

The method is well-suited for the study of cellular migration, proliferation, growth, and differentiation, as well as a multitude of biochemical and biophysical events. It also opens up new possibilities for highly spatially resolved distribution of nanoparticles, drugs, genes and different biochemical markers, such as dyes into single cells or organelles both isolated and in situ. The method may be useful in clinical applications as a vehicle to administer drugs and genes to patients.

In another non-limiting aspect the method can be used to transfer organelles or cells to the cytoplasm of other cells or to tissues.

The method can be used for high throughput, parallel and/or sequential alteration of the chemical content of cells and cellular structures. The cells and/or cellular structures may be disposed in a plurality of spots in separated wells or in one larger-sized container or on a substrate (e.g., glass slide, plastic or polymer surface, membrane, microfluidic chip, and the like).

In one aspect, the method comprises providing at least one tip-electrode, preferably together with at least one ground electrode. The at least one tip-electrode is filled with an electrically conductive medium such as a liquid or gel comprising electrolytes and is in electrical communication with a current or voltage generator In one aspect, an electric pulse is applied between at least one tip-electrode and a counter or ground electrode using a current- or voltage-generator, generating an electric field focused on at least one cell or cellular structure essentially without affecting any surrounding cells or cellular structures.

The electrical field is of a strength sufficient to obtain dielectric breakdown and pore formation in the membranes of the at least one cell or cellular structure. Preferably, the pulse generator in communication with the tip-electrode generates an electric pulse or a pulse train, either as voltage or as current, that gives rise to an electric field strength that is from about 0.1 kV/cm to 10 kV/cm at the surface of the cell structures to be electroporated, and more preferably it is from about 0.5 kV/cm to 1,5 kV/cm at the surfaces. The electric field can be delivered as a single pulse, or as a pulse train of several pulses. Preferably a pulse is from about 0.1 µs to several minutes (e.g., about 1-10 minutes). More preferably a pulse ranges from about 1 µs to 5 s, and most preferably it is less than about 100 ms. The number of pulses is preferably between about 1 and 1000, and more preferably between about 1 and 50. When more than one pulse is used, the interval between the pulses is preferably from about 0.1 µs to several minutes, and more preferably between about 1 µs and 5 s.

In one aspect, the electrically conductive medium comprises an agent (such as a membrane-impermeant molecule) that can be delivered from the medium through the target-facing opening of the tip-electrode to the surface of the target cell(s)/cell structure(s). Agent is delivered through the opening and is transported through pores in cell membranes generated by exposure to the electric field produced by the tip-electrode. Delivery of the agent may occur simultaneously, prior to or after exposure to the electric field. Additional exposures to electric fields may transport agents further into the cell structures or may permit additional agents of the same or different type to be introduced into the cell structures and/or residual agent remaining at the surface of the cell structure to be introduced.

If two or more tip-electrodes are employed, tip electrodes are preferably aligned vertically to the same height. In certain aspects, one or more of the tip-electrodes is movable in three-dimensional space, independently of each other, e.g., using independently controlled micropositioners. In another aspect, two or more tip-electrodes are independently movable in a z-direction (e.g., through positioning mechanisms provided on an electrode plate as discussed above) but are otherwise fixed in x- and y-directions, moving as one as the electrode plate is moved.

The method of the invention may be used for transferring multiple solutes, agents, and particles into permeabilized cell structures to determine the effects of such introduction.

Methods for Intracellular Delivery of Agents

The methods of the invention can be used to facilitate high throughput, parallel screening of intracellular drug actions or intracellular drug targets, as a technique for transfection, or for identification of intracellular proteins and signaling pathways. Examples of such proteins can be enzymes, receptors, carriers, or structural proteins. In these instances, the electroporation technique is used for, e.g., introduction of one or several protein probes (such as fluorogenic ligands or substrates) into cells. These probes can be introduced alone or in combination with drugs, substrates or ligands, inhibitors, agonists, agonists, and other molecules, that interact directly with a target protein or proteins in the same signaling pathway. Thus, both the presence of various proteins and their function can be determined at the single-cell level or on the level of populations of cells.

To use the invention for profiling, screening, alteration, and probing of interactions of intracellular biomolecules, such as proteins, or drug actions inside living cells, events related to these interactions must be rendered detectable. This can be achieved by, for example, through the use of selective fluorescent protein markers in combination with fluorescence microscopy or fluorescence plate reading systems. As an example, to verify the presence of a certain enzyme inside a cell, a polar cell-membrane-impermeant substrate that is non-fluorescent can be used that converts into a fluorescent product after enzyme action. An increase in fluorescence reflects the presence of the enzyme and can be used to measure enzymatic activity. Similarly, the method may be used to perform a FRET-based analysis of protein-protein interactions, interactions between proteins and nucleic acids, and interactions between nucleic acids and other nucleic acids. However, a number of electrical and optical methods can be used to detect the cell response after internalization of an agent including but no limited to capacitance, voltametry, amperometry, CARS (coherent anti-stokes raman scattering), SERS (surface-enhanced raman scattering), phosphorescence, chemoluminescence, UV-VIS-IR absorption, quartz crystal microbalance, and surface plasmon resonance.

With this method, single or multiple cell-loading agents can be transferred in a single, parallel or sequential mode to a population of cells, cellular structures, single cells or, single cellular structures (target(s)). More specifically, the disclosed method uses a single or a plurality of tip-electrodes coupled to an electric field generator for electroporation of a target(s), by positioning the single or plurality of tip-electrodes in the close vicinity of the target(s). At least one current or voltage pulse is transmitted through the tip-electrode(s) generating an electric field, which causes formation of pores in the membrane(s) of the target(s).

Single or multiple cell-loading agents contained in the single or plurality of tip-electrodes are delivered at the site of pore formation either by the electrophoretic and/or electroosmotic flow created in the single or plurality of tip-electrodes during the electric field pulse or through flow created through, for example, hydrodynamic pumping, allowing the single or multiple cell-loading agents to translocate the membrane and enter the interior of the target(s) through the pores.

The cell-loading agents are preferably added to the electrolyte-containing solution in the tip electrode(s). In addition, the tip-electrodes may be supplemented with drugs, or agents, for interacting with targets located in the cell plasma membrane. Such targets include plasma-membrane-bound receptors and enzymes.

When systems of the invention are used for intracellular screening applications (discussed further below), preferably, a plurality of different cell-loading agents are introduced to the cytosol of one or several cells, and/or cellular structures, in a controlled fashion. Screening is preferably achieved using parallel or sequential delivery of loading agents to the cellular target and may, for example, be accomplished by one of the following embodiments.

Of the first embodiment, parallel and sequential delivery of multiple cell-loading agents is achieved using arrays of tip-electrodes. The arrangements of tip-electrodes can be one-dimensional arrays (linear), or two-dimensional arrays. Preferably arrays of 2-100,000 tip-electrodes are used, and most preferably 8, 96, or 384 tip-electrode-arrays will be employed in order to suit standard microtiter-plate formats.

Parallel delivery means introduction of agents by electroporation into a plurality of groups of cells or single cells using a plurality of tip-electrodes. Parallel delivery can be achieved by placing the array of tip-electrodes over cellular targets in separate containers, so each tip-electrode causes electroporation and subsequent delivery of one type of loading agent or mixture of several loading agents to the cellular target. The parallel treatment can be followed by another parallel treatment with a new type of loading agent or mixture of several loading agents to the cellular target. It can also be achieved by placing the array of tip-electrodes over cellular targets in one large container, e.g., where the cellular targets either is a confluent cell culture or cells grown in desired patterns.

To achieve sequential delivery of loading agents in this embodiment of using tip-electrode arrays, each tip-electrode contains one or different types of cell-loading agent or a mixture of several cell-loading agents. Sequential delivery can be achieved by moving the array of tip-electrodes over a single cellular target in sequence, each tip-electrode causing electroporation and subsequent delivery of each type of cell-loading agent or mixture of several cell-loading agents.

Instead of moving the array of tip-electrodes, it is also possible to move the cell structures in relation to spatially fixed tip-electrodes. It is also possible to use the same kind of set up, where each tip-electrode contains one or different types of cell-loading agent or a unique mixture of several cell-loading agents, but instead of performing sequential delivery to the same cellular target, the cell-loading agents are delivered to separated cellular targets and thereby give rise to cellular targets with individual loading agents internalized.

In one embodiment, the agents to be loaded into the cells can be aspirated into the tip-electrodes (front loading) using commercially available pipetting technology, either integrated into a robotic device or some other dispensing system. In another embodiment, where the tips are integrated into a device, the agents can be aspirated as described above, or, if there are channels in the device and the channels are connected to at least one external vial, the agents can be loaded through the upper tip inlet (back-loading). The combination of pore formation and delivery of agents supplemented to the electrolyte-solution in the tip-electrode, enable loading of materials into the cytoplasm of a small population of cells or single cells.

It is sometimes preferable to load the tip-electrodes from the tip end/bottom outlet using capillary forces or aspiration/suction. This procedure can be used to load a plurality of tip-electrodes simultaneously. The tip-electrodes are positioned in individual vials containing cell-loading agents and a small sample is introduced into the tip-electrode using any of the above mentioned methods.

Of the present invention, the method thus enables parallel agent delivery in combination with electroporation. Because the tip-electrode arrays discussed in the embodiments above for sequential delivery of cell-loading agents also are ideally suited for electroporation of cells grown in patterns on a surface or cells contained in multiple wells in a multi-well plate, the present invention provides a tool for parallel intracellular screening applications. In parallel delivery of a cell-loading agent, each single tip outlet in an array of tip-electrodes targets a population of cells or single cells on a surface or in a well structure. Thus, individual cells or small populations of cells can be targeted with the same, or different, compounds that are internalized into the cytoplasm simultaneously. Thus, any of the embodiments for sequential agent delivery, as discussed above, may be employed for electroporation of multiple cell structures.

The present invention may be used for internalizing agents into cells using electroporation comprising any of the following non-limiting methods:

1. Intracellular delivery of membrane-impermeant agents to a population of cells or a single cell of one cell type.
2. Intracellular delivery of membrane-impermeant agents to physically separated cells in a population of cells or single cells of the same cell-type.
3. Intracellular delivery of membrane-impermeant agents to physically separated cells in population of cells or single cells of different cell-types.
4. Sequential intracellular delivery of membrane-impermeant agents to a population of cells or a single cell of one cell type.
5. Sequential intracellular delivery of membrane-impermeant agents to physically separated cells in a population of cells or single cells of the same cell-type.
6. Sequential intracellular delivery of membrane-impermeant agents to physically separated cells in a population of cells or single cells of different cell-types.
7. Parallel intracellular delivery of membrane-impermeant agents using several tip-electrodes to a population of cells or single cells of one cell type.
8. Parallel intracellular delivery of membrane-impermeant agents using several tip-electrodes to physically separated cells in a population of cells or single cells of the same cell-type.
9. Parallel intracellular delivery of membrane-impermeant agents using several tip-electrodes to physically separated cells in a population of cells or single cells of different cell-types.
10. A combination of parallel and sequential intracellular delivery of membrane-impermeant agents using several tip-electrodes to a population of cells or single cells of one cell type.
11. A combination of parallel and sequential intracellular delivery of membrane-impermeant agents using several tip-electrodes to physically separated cells in a population of cells or single cells of the same cell-type.
12. A combination of parallel and sequential intracellular delivery of membrane-impermeant agents using several tip-electrodes to physically separated cells in a population of cells or single cells of different cell-types.
13. Any mode of intracellular delivery of membrane-impermeant agents described above (1-12) used in combination.

Applications

Important applications of the method of the present invention, include its use in drug screening, protein identification, and loading cells with therapeutic agents. In particular, by applying a permeabilizing electric field over cells or cellular structures, specific probes (markers), substrates or ligands can be introduced into the cytoplasm to screen for intracellular chemistry such as cytosolic enzymes and receptors on organelles. More specifically, this facilitates screening of intracellular drug action as well as assaying of intracellular proteins such as enzymes, receptors or structural proteins. Using the method of the present invention, these markers can be introduced in combination with drugs or ligands that interact directly with the target protein or proteins in the same signaling pathways. Thus, with the present invention it is possible to characterize, even on the single cell level, both the presence of various proteins and their function. Blocking of particular pathways with specific ligands, antagonists, inhibitors or modulators might enable control of cellular processes and provide leads for novel systems. Such compounds can be introduced to a cell, for example, by co-electroporating them using a tip-electrode containing the one or several ligands of interest. Alternatively, they may be internalized in a cell structure by other means, for example, cell-permeable agents may be employed. The method is also highly suitable to modify and/or detect nucleic acids such as DNA and RNA present in cells, as well as to transfect cells with nucleic acids such as DNA, RNA, iRNA, and antisense oligonucleotides.

In general terms, the method of the invention can be used in the following, non-limiting, areas of applications: proteomics, genomics, phenotype profiling (phenomics), drug assays and screening, pharmacokinetics, in vitro fertilization, transgenics, nuclear transfer, organelle transfer, and diagnostics. More specific, but still non-limiting, applications in which the method of the invention can be used are gene transfection, gene identification, enzyme identification, protein identification, receptor identification, binding assays, enzyme assays, competitive enzyme assays, non-competitive enzyme assays, enzyme assays with modulators, enzyme assays with isosteric inhibitors, receptor assays, receptor assays with antagonists, receptor assays with modulators, viral assays, bacterial assays, drug assays, kinetic assays, modification of metabolic pathways, and modification of signaling pathways.

Specifically, the method of the invention is very suitable for identification of intracellular receptor and receptor ligands. Intracellular receptors and ion channels that cause release of signaling molecules such as $Ca^{2+}$, cAMP, $K^+$ etc. can be identified and studied using ligand libraries that are electroporated into cells, preferably in combination with selective receptor antagonists. For example, $Ca^{2+}$ released from intracellular stores upon activation of an intracellular receptor can be detected using fluorogenic chelating agents such as magfura-2 and fluo-3.

Furthermore, to identify the receptor, or to reveal receptor-ligand interactions, a selective receptor antagonist may be used and electroporated into the cell to selectively block the action of the ligand. In addition to fluorescence probes, radio ligands, blotting or electrophysiological methods, and fluorogenic substrates can be used. Fluorogenic markers are often cell-permeant esters that can be added to the cell bath medium and need not be electroporated into cells. Thus, using such esters, cells can be loaded with dyes before electroporation experiments. By having the ability to introduce both a receptor agonist in addition to a marker for the specific receptor activation it is possible to, for example, identify the most potent receptor agonist from a library of agonists or the most potent antagonist from a library of antagonists.

It is also possible to design experiments to obtain, for example, dose-response curves. For example, with the method of the present invention it is possible to introduce both a receptor agonist and a receptor antagonist into the cell cytosol at different concentrations of the respective compound in addition to a marker for the specific receptor activation. It is also possible to introduce both a receptor agonist and a receptor antagonist into the cell cytosol at different concentrations of the respective compound with the overall aim to find out the nature of the receptor agonist and the receptor antagonist binding, i.e., whether it is competitive or non-competitive, etc. In addition to identification of receptors, and ligands also so-called "ligand fishing" or "de-orphaning" can be performed in this way. A cell with a known set of receptors is used as detectors and a library of potential samples of ligands are introduced to the cell cytosol to screen for the actions of these ligands.

Furthermore, the invention is suitable for identification of intracellular enzymes and enzyme substrates. Highly specific enzyme substrates that result in fluorescent products can be used for protein/enzyme identification in, for example, proteomics and phenotype profiling of individual intracellular systems using the technique of the invention. The synthetic substrate, possibly in combination with a drug, inhibitor, or modulator, can be introduced into the cell using electroporation of the present invention. There are a variety of substrates available that can be employed as light switches in the substrate-product conversion step. Such substrates include substrates for esterases, sulfatases, phosphatases, and so on. Either the substrate is fluorescent and the product is non-fluorescent or vice versa.

For coupled reaction systems within cells, for example, the degradation of alcohol by the alcohol dehydrogenase that utilize the conversation of $NAD^+$ to —NADH, thus causing a shift in fluorescence, the target molecule need not be fluorescent as long as it is coupled to a reaction that yields a detectable molecule. Other examples of such native fluorescent compounds in cells are NADPH and flavines.

Chemical amplification with enzymes can also be used to increase the sensitivity of the system (Blaedel, et al., in H. U. Bergmeyer (ed) *Methods of Enzymatic Analysis*, verlag Chemie/Academic Press, New York 1974 vol 1, p 131). The principle of this method is to use enzymes that turn the substrate into products, and thus cause a large concentration change from substrate, which may be difficult to measure, into products, which can be readily measured.

One example of a fluorogenic substrate is fluorescein diphosphate (FDP) that can be used for detection of phosphatases. The substrate is hydrolyzed by alkaline phosphatase and yield the fluorescent product fluorescein. Another system is the casein-BODIPY FL, which is substrate for metallo-, serine, acid and sulfhydryl proteases, including cathepsin, chymotrypsin, elastase, papain, pepsin, thermolysin and trypsin. Other examples of systems are β-galactosidase where the substrate is fluorescein di-β-D-galactopyranoside (FDGP) which is sequentially hydrolyzed by β-galactosidase, first to fluorescein monogalactoside (FMG) and then to highly fluorescent fluorescein.

FIGS. 14A-E show the experimental result of using fluorescein diphosphate (FDP) to target the intracellular enzyme alkaline phosphatase that catalytically hydrolyses the phosphoester-bonds on the substrate so that the highly fluorescent product fluorescein is formed in the cytosol. The substrate fluorescein diphosphate (FDP) was supplemented to the electrolyte in the tip-electrode and transferred into the cell during electroporation. The substrate is non-fluorescent and the product is fluorescent. The fluorescence obtained in the cells in FIGS. 14B and E, which indicates the presence of the product, signals also the presence of the enzyme.

Protein-protein interactions are complex and involve many processes. Blocking of particular pathways with specific ligands might enable control of cellular processes and provide leads for novel systems (Zutshi, et al., *Curr. Opin. Chem. Biol.* 2: 62-66, 1998). For example, the intracellular protease activity was investigated using a protein, casein, which was heavily loaded with the green-fluorescent molecule BODIPY FL as enzyme substrate. In solution, casein-BODIPY FL is folded so that the quatemary arrangements in the molecule quench the fluorescence. When the peptide bonds are cleaved, by the action of cytosolic proteases, segments of free peptides tagged with BODIPY FL starts to fluoresce.

The method might also be used in combination with application of drugs and agents that affect receptors situated on the cell plasma membrane. Thus, both surface receptors and intracellular (cytoplasmic) interactions of one or several drugs can be probed simultaneously, and used, e.g., as a method to characterize signaling pathways.

Electroporation of individual organelles also can thereby be accomplished using the tip-electrodes according to the invention. Even spatially well-defined intracellular domains with a targeted class of organelles can be held under a localized electric field with this invention, thereby enabling transfer of polar solutes into organelles. Applications of electroporation of organelles include alterations of the mitochondrial genome. It is well known that mutations in the mitochondrial genome can lead to a multitude of diseases, and that gene therapy can potentially be of major importance. So far, however, mitochondria has to be isolated from the cells before transfer of the new gene fragment into the mitochondria can be performed. Then, the mitochondria has to be reinserted into the cell. The technique according to the invention makes it possible to directly insert genes into the mitochondria when they are contained inside a cell. This is a significant advancement over traditional schemes for transfection of mitochondria.

The organelles can be contained inside a single cell or they can be isolated from a single cell or a population of cells. In such applications, the strengths of the pulse provided by a pulse generator in communication with tip electrode(s) depend on what structure to be electroporated and on the distance between the electrodes. Small organellar structures, like endoplasmic reticuli, and mitochondria, require a higher voltage to create pores in the membrane. The pulse duration can also be varied in the range of a few microseconds to several minutes depending on membrane structure but also on the structure of the compound to be incorporated. Large molecules with low diffusion rates require longer periods of time to move into the cell. For electroporation of organelles inside a cell, tip electrodes preferably have electrically insulating shanks, so that the part of the electrode that comes into contact with the cell membrane does not result in electrically-induced pore-formation. The physical dimensions of intracellular electrodes for electroporation of organelles can range from a few nanometres to a few micrometers in diameter.

Preferably, tip electrodes are arranged so that the organelle to be permneabilised is located between the electrodes while an electric field of sufficient strength is applied. An organelle impermeant molecule may be introduced into the organelle through the lumen of one or both tip electrodes. This procedure is repeated until the desired number of organelles have been permeabilised. Excess molecules may be removed from the cytoplasm using degradative pathways, or by some other means, and the molecules are exclusively located inside a population of permeabilised organelles.

Another application of the present invention is for use with biosensor techniques. In particular, by applying a permeabilising electric field over a single cell, intracellular chemistry and organelles can be used for biosensing purposes. As an example, inositoltriphosphate, which activates receptors on endoplasmic reticuli, can be assayed for using such schemes. The compound is simply added to the buffer surrounding the permeabilised cell and will diffuse into the cell interior and bind to receptors on endoplasmic reticuli. Upon binding of inositoltriphosphate to the receptors, endoplasmic reticuli will liberate calcium ions. If the cell is then supplemented with a fluorogenic calcium chelating dye, such as fluo-3, the receptor activation can be measured as an increase in fluorescence.

When tip-electrodes are used, according to the present invention, the cell-impermeant molecules added to the non-solid electrically conductive medium can be administered to the cell using a perfusion system, such as a microsyringe pump or a peristaltic pump. According to another scheme, the cell-impermeant molecules contained in the electrolyte solution can be delivered to a cell using electrophoresis or electroosmosis. An applied electric field causes pore formation in the cell as previously discussed. Because the components inside the electrode electrolyte will be separated based on their charge-to-frictional drag ratio, this opens up possibilities for performing organelle-sensor-based detection of species fractionated by electrophoresis.

If the methods according to the invention are carried out in vivo it is possible to use a surgical microscope in order to view the cell structure. Furthermore, it is possible to use a stereotactic device for the positioning of the tip-electrodes. When the method is performed in vivo it is of course not possible to place the cell structure in some sort of container with buffer. Instead, the compound to be incorporated into the cell structure is administered in a physiological buffer either separately via a catheter or directly via a hollow fibre electrode. When a tip-electrode is used, the compound is administered to the cell structure through the opening of the target-facing end of the tip electrode. The receiving end of the tip electrode is coupled to a fluid delivery system, such as a syringe controlled by a micrometer screw or a microinjection pump to enable administration of an exact volume.

The possibilities to add the compound either at the same time as the electroporation occurs or with some time delay make this technique very useful. A very high concentration is achieved locally at the selected cell and diffusion into it will be faster due to the greater concentration gradient. The lower consumption of the compound and the minimization of the problems due to the washing procedure are some other advantages. Many times a focal administration, i.e., administration directly to the malfunctioning set of cells, of drugs or genes can be expected to be far superior than intraperitoneal, oral, intraventricular, or any other kind of commonly employed drug-administration technique.

Intracellular drug-and-gene-administration in vivo can be accomplished with the method according to the invention. Because of the extremely small dimensions of the electrodes, in combination with the low voltages applied, very little tissue trauma is expected. Furthermore, the positioning of the electrodes and the subsequent gene or drug delivery is very precise. It has been shown that microdialysis probes, which are on the order of a hundred times larger than the electrodes used in the method according to the present invention, cause very little tissue trauma and disruption of local metabolism.

With the method according to the invention, used in combination with gene therapy, it will be possible to "re-program" cells; either in order to make a malfunctioning cell work in the correct way, or to give a cell a new function.

It is thus possible to use the method according to the invention in therapies for and treatment of different diseases and conditions caused by the malfunction of single cells or a small population of cells, such as Parkinson's disease and brain tumours, which is further illustrated below.

Many diseases whether genetically acquired or not, result in metabolic disruptions. For example, Parkinson's disease caused by degeneration of neurons in the Nigro-striatal pathway result in malfunctioning in the biochemical machinery for production of dopamine in an isolated population of cells. This in turn results in motor/behavioral deficits. The standard treatment of Parkinson's disease is by oral administration of L-DOPA, a precursor of dopamine. Alternatively, grafted tissue with neuronal cells producing dopamine is transplanted into the patient's brain. Intracellular drug or gene administration in vivo into the appropriate brain structures can be accomplished using an electroporation procedure similar to that described in the two above examples and used as a therapeutic strategy.

Experimental treatment of brain tumors using genetically engineered viruses for gene delivery has been used with anecdotal reports of success. The use of viruses as a delivery system has limitations in that it might pose a potential hazard if the virus mutate. Using an electroporation procedure for gene delivery, e.g. "suicide genes" for cytokine deaminase or thymidine kinase, similar to that described in the examples below, eliminates the need for the use of virus delivery systems in cancer therapy.

The positioning of tip electrodes can be performed using a stereotactic atlas, in the figure represented by the Cartesian co-ordinate system, and stereotactic micropositioners. Perfusion can be achieved as shown in the figure with a syringe or by some other appropriate means. The positioning of the electrodes and the applied electrical field can be varied so a desired number of cells are electroporated.

The agents to be electroporated into cells are then simply administered through the narrow channel in the centre of the electrode or electrodes by application of a flow by means of a syringe pump or a peristaltic pump or any other type of solution pumping system including electrophoresis.

An especially interesting possibility is to use battery-operated perfusion/electroporation implants in biotolerable materials for continuous application of solutes into cells. Because such low potentials are required, batteries providing voltages in the range of from a few to about 20 volts can be used. These battery-operated electroporation units can be made small, they can be included on a chip measuring only a few millimetres squared. Such a system could include a solute-containing solution reservoir, two electrodes for electroporation, electronic circuitry for timed delivery and control of the electroporation parameters, i.e. pulse profile, pulse duration, repeat, and amplitude as well as a battery source, and a reservoir refill inlet.

When the method according to the invention is used for transferring entrapped solutes out of cell structures, so called reversed electroporation, some of the applications are drug delivery to single cells or small populations of cells. This is, e.g., used in order to permeabilise cells and cell-like structures, such as liposomes in order to transfer cell impermeant solutes from their inside to the extracellular media. The concentration gradient for the solutes then have the opposite direction i.e. high solute concentrations inside the cell structure and low solute concentrations outside the cell structure. In particular, liposomes with entrapped drugs can be emptied in a controlled way close to a target cell simply by applying a DC voltage pulse over its membrane through carbon fibre tip-electrodes positioned in the same way as described above. The use of such liposome-based delivery of drugs triggered by electroporation can be used in basic research as well as in the pharmaceutical industry, e.g., for compositions with delayed release.

EXAMPLES

The invention will be further illustrated in the examples below, which in no way limit the scope of the invention.

Example 1

Electroporation of a Single Spot of Cells in a Confluent Culture galactosidase, PC-12 cells were cultured of standard procedures in conventional petri dishes. The cell culturing media was removed and replaced with a Hepes Saline buffer, pH 7.4, and the cell culture were transferred to the stage of an inverted microscope (Leica, model DMIRB equipped with a x-y translational stage). A tip-electrode manufactured from a conventional pipette tip with a platinum wire inserted horizontally to the interior of the tip, was filled with Hepes-saline buffer supplemented with 500 µM Fluorescein diphosphate (FDP). The tip-electrode was connected to a pulse generator (AM-systems isolated pulse stimulator, model 2100) via an oscilloscope for monitoring of the pulse. A counter electrode in the cell bath was connected to ground and the sign of the potential in the tip-electrode was negative. The outlet of the tip-electrode were positioned at a distance of 50 µm above the cell culture. The cells were exposed to 5×10 pulses of 100 ms duration, with a 100 ms delay time between pulses of 3 mA amplitude. FDP was transferred out of the tip-electrode by electroosmotic forces, no additional pressure or pumping were added to the system. Internalization of FDP were detected, after splicing of FDP to fluorescein in the cytosol of the cells by unspecific phosphatases, by the fluorescence system of the microscope, collected by a digital CCD camera and stored by a fluorescence imaging software. The result is presented in FIG. 13A. As is seen in the figure, the cells situated under the tip-electrode wall has been successfully electroporated and expose a bright fluorescence. This is due to the high electric field strength created at the interface between the grounded cell bath and the homogeneous electric field inside the tip-electrode. Approximately 500 cells has been targeted and successfully electroporated in this experiment.

Example 2

Parallel Electroporation of Spots in a Confluent Cell Culture PC-12 cells were cultured of standard procedures in conventional petri dishes. The cell culturing media was removed and replaced with a Hepes Saline buffer, pH 7.4, and the cell culture were transferred to the stage of the inverted microscope. Two tip-electrodes, connected to the pulse generator via a single rod inserted through both tips, were filled with Hepes-saline buffer supplemented with 500 µM Fluorescein diphosphate (FDP). One counter electrode was placed in the cell bath and connected to ground. The outlet of the two tip-electrodes were positioned at a distance of approximately 100 µm above the cell culture. Two spots of cells, under the two tip-electrodes, were exposed to 4×10 pulses of 100 ms duration, with a 100 ms delay time between pulses of 4 mA amplitude. FDP was transferred out of the tip-electrodes by electroosmotic forces, no additional pressure or pumping were added to the system. Detection and imaging were performed in the same way as in the previous example. The result is presented in FIG. 14C-E. Both areas situated right under the tip-electrodes has been successfully electroporated and FDP has been internalized into the cells. The distance between the two tip-electrodes is approximately 2 mm, and as can be seen in the figure, this distance can substantially be reduced.

Variations, modifications, and other implementations of what is described herein will occur to those of ordinary skill in the art without departing from the spirit and scope of the invention.

All of the references, patents, patent applications, patent publications and international applications identified herein are incorporated herein in their entireties.

What is claimed is:

1. A tip-electrode comprising:
   a housing defining a lumen for receiving an electrically conductive medium; and an electrically conducting surface for coupling to a voltage or current generator, wherein the electrically conducting surface comprises a structure conformed to fit into the housing defining the lumen of the tip-electrode.

2. The tip electrode of claim 1, wherein the housing comprises a target-facing end comprising an opening in communication with the lumen for delivering an agent through the opening to a target.

3. The tip electrode of claim 1, wherein the lumen comprises an electrically conductive medium.

4. The tip electrode of claim 1, wherein the housing comprises a tapered end.

5. The tip electrode of claim 1, wherein the electrically conductive surface is of the form of a cylinder, rod, filament, or wire.

6. The tip electrode of claim 5, wherein the electrically conducting surface is a structure penetrating the walls of the housing on one or both sides of the housing.

7. The tip electrode of claim 1, wherein the electrically conducting surface is a wire connected on the outside of the housing to a ring plate.

8. The tip electrode of claim 1, wherein the electrically conductive medium is a liquid.

9. The tip electrode of claim 1, wherein the electrically conductive medium is a gel.

10. The tip electrode of claim 1, wherein the electrically conductive medium comprises an agent for delivery to a target.

11. The tip electrode of claim 1, wherein the housing comprises a material selected from the group consisting of glass, fused silica, plastic, ceramic, an elastomeric material, a polymer, metal, a non-conducting material coated at least partially with a conducting material, and a conducting material coated at least partially with a non-conducting material.

12. The tip electrode of claim 2, wherein the housing further comprises a receiving end distal to the target-facing end and comprises an opening for receiving the electrically conductive medium.

13. The tip electrode of claim 1, wherein the tip-electrode further comprises a conducting surface which functions as a counter electrode.

14. The tip-electrode of claim 1, wherein the housing comprises a uniform inner diameter and uniform or varying outer diameter.

15. The tip-electrode of claim 1, wherein the housing comprises a uniform outer diameter and uniform or varying inner diameter.

16. The tip-electrode of claim 1, wherein the length of the tip electrode is less than about 10 cm.

17. The tip-electrode of claim 1, wherein the length of the tip electrode is less than about 500 mm.

18. The tip-electrode of claim 1, wherein the length of the tip electrode is less than about 50 mm.

19. The tip-electrode of claim 1, wherein the length of the tip electrode is less than about 1 mm.

20. The tip-electrode of claim 2, wherein the diameter of the opening at the target-facing end is less than or equal to about 5000 mm.

21. The tip-electrode of claim 2, wherein the diameter of the opening at the target-facing end is less than about 100 mm.

22. The tip electrode of claim 2, wherein the diameter of the opening at the target-facing end is less than about 50 mm.

23. The tip-electrode of claim 2, wherein the diameter of the opening at the target facing end is less than about 10 mm.

24. The tip-electrode of claim 2, wherein the diameter of the opening at the target-facing end is less than about 1 mm.

25. The tip-electrode of claim 2, wherein the diameter of the opening at the target-facing end is less than about 100 nm.

26. The tip-electrode of claim 2, wherein the diameter of the opening at the target-facing end is less than about 50 nm.

27. An electrode plate comprising at least one mounting point for receiving a tip electrode, wherein tip electrode comprises a housing defining a lumen for receiving an electrically conductive medium and an electrically conducting surface for coupling to a voltage or current generator.

28. The electrode plate of claim 27, wherein the at least one mounting point comprises a flexible attachment point for receiving the tip electrode permitting vertical movement of a tip-electrode from the mounting point.

29. The electrode plate of claim 27, comprising a plurality of mounting points.

30. The electrode plate of claim 29, wherein the plate comprises a row of mounting points for forming a linear array of tip-electrodes.

31. The electrode plate of claim 29, wherein the plate comprises a plurality of rows of mounting points for forming a two-dimensional array of tip-electrodes.

32. The electrode plate of claim 29, wherein the center-to-center distance of each mounting point corresponds to the center-to-center distance of wells in a microtiter plate.

33. The electrode plate of claim 27, wherein the electrode plate comprises at least one interface point for a voltage or current generator.

34. The electrode plate of claim 27, wherein the electrode plate comprises at least one interface point for interfacing with a fluid delivery device.

35. The electrode plate of claim 27, wherein the electrode plate comprises at least two layers including a conducting layer and an insulating layer.

36. The electrode plate of claim 27, wherein the at least one mounting point comprises an aperture for receiving the tip-electrode.

37. The electrode plate of claim 36 or 35, comprising a layer that functions as a counter electrode.

38. The electrode plate of claim 27, wherein at least one tip-electrode is mounted to the electrode plate at the mounting point.

39. The electrode plate of any of claims 29-31, wherein a plurality of tip electrodes are mounted to the electrode plate.

40. The electrode plate of claim 27, wherein the plate comprises at least one microfluidic channel for delivering fluids to at least on tip electrode mounted to the plate.

41. A tip-electrode plate comprising a substantially planar plate on which at least one non-planar element is fabricated thereon, the non-planar element comprising an electrically conductive medium and wherein the end of the non-planar element distal from the plate comprises an opening for exposing a target to an electric field and for the delivery of an agent from the opening to the target, and wherein inner walls of the non-planar element define a lumen.

42. The tip-electrode plate of claim 41, wherein the inner walls comprise an electrically conductive surface and the lumen comprises an electrically conductive medium.

43. The tip-electrode plate of claim 42, wherein the electrically conductive surface is a conductive coating which at least partially coats the inner walls of the reservoir.

44. The tip-electrode plate of claim 41, further comprising an electrically conductive surface comprising a wire, rod or filament at the base of the lumen or which penetrates one or both walls of the non-planar element.

45. The tip electrode plate of claim 41, wherein the end of the at least one non-planar element is tapered.

46. The tip electrode plate of claim 41, wherein the plate comprises a first layer comprising a plurality of reservoirs and a substantially planar second layer comprising a plurality of nonplanar elements elevated above the plate, wherein each nonplanar element comprises a target-facing opening centered above each reservoir in the first layer for exposing a target to an electric field, and wherein inner walls of the nonplanar element define a lumen communicating both with the reservoir and the opening.

47. The tip-electrode plate of claim 46, wherein the plate further comprises a counter electrode layer.

48. The tip electrode plate of claim 41 or 46, wherein reservoirs comprise an electrically conductive medium.

49. The tip electrode plate of claim 48, wherein the electrically conductive medium comprises an agent.

50. The tip electrode plate of claim 47, wherein the counter electrode layer contacts the electrically conductive medium.

51. The tip electrode plate of claim 41 or 46, wherein the reservoirs comprise an agent.

52. A kit comprising a tip electrode of claim 1 and a container for containing a target.

53. A kit comprising an electrode plate of claim 27 and at least one tip electrode for mounting on the electrode plate.

54. The kit of claim 53, further comprising a container for containing a target.

55. The kit of claim 53, wherein the electrode plate comprises at least on microfluidic channel.

56. The kit of claim 54, wherein the electrode plate and/or container comprises at least one microfluidic channel.

57. The kit of claim 54, wherein the container for containing the target is selected from the group consisting of a microtiter dish, a multi-well cell culture container, a petrie dish, polymeric substrate, a glass substrate, a microfluidic chip, and a membrane.

58. The kit of claim 53, wherein the kit further comprises at least one counter electrode.

59. The kit of claim 53, wherein the kit further comprises an electrically conductive medium for filling at least one tip-electrode.

60. The kit of claim 53, wherein the kit comprises at least one agent.

61. The kit of claim 53, wherein the kit comprises at least one cell.

62. A kit comprising a tip-electrode plate of claim 53, wherein the kit further comprises container for containing a target.

63. The kit of claim 62, wherein the tip-electrode plate and/or container further comprises at least one microfluidic channel.

64. The kit of claim 63, wherein the container for containing the target is selected from the group consisting of a microtiter dish, a multi-well cell culture container, a petrie dish, polymeric substrate, a glass substrate, a microfluidic chip, and a membrane.

65. The kit of claim 63, wherein the kit further comprises an electrically conductive medium for filling at least one reservoir.

66. The kit of claim 63, wherein the kit comprises at least one agent.

67. The kit of claim 63, wherein the kit comprises at least one cell.

68. A system comprising at least one tip electrode comprising:
an electrically conducting surface in contact with an electrode plate and a housing defining a lumen for receiving an electrically conductive medium, wherein the housing comprises a target-facing end comprising an opening in communication with the lumen for delivering an agent through the opening to a target, wherein the electrode plate is connectable to a pulse generator for delivering a voltage or current pulse to the electrically conducting surface.

69. The system of claim 68, further comprising:
a container for containing a target.

70. The system of claim 68, wherein the system further comprises a mechanism for positioning the at least one tip-electrode in proximity to a target.

71. The system of claim 68, wherein the system further comprises a pulse generator in communication with the electrode plate for delivering voltage or current pulses through the at least one tip electrode.

72. The system of claim 68, further comprising at least one counter electrode.

73. The system of claim 68, wherein the lumen of the at least one electrode tip comprises an electrically conductive medium.

74. The system of claim 73, wherein the electrically conductive medium comprises an agent.

75. The system of claim 73, wherein the system further comprises a delivery mechanism for delivering a fluid and/or an agent to at least one tip electrode.

76. The system of claim 75, wherein the delivery mechanism further comprises one or more of: a pumping mechanism, a mechanism for electroosmosis, or a mechanism for electrophoresis of an agent through the lumen of the tip electrode.

77. The system of claim 68, wherein the system comprises a plurality of tip electrodes, each in electrical contact with the electrode plate.

78. The system of claim 77, wherein electrical pulses transmitted through each tip electrode are independently controlled through a system processor.

79. The system of claim 77, wherein the plurality of tip electrodes are arrayed in a row.

80. The system of claim 77, wherein the plurality of tip electrodes arrayed in a plurality of rows.

81. The system of claim 71 or 77, wherein the electrode plate and/or container comprise one or more microfluidic channels.

82. The system of claim 68, wherein the system further comprises a detector, for detecting alteration of electrical properties or optical properties of a target proximity to a tip electrode and/or delivery of a fluid and/or agent to the target.

83. The system of claim 68, wherein the at least one tip electrode is detachable from the electrode plate.

84. The system of claim 68, wherein the at least one tip-electrode is an integral part of the electrode plate.

85. The system of claim 84, wherein the electrode plate comprises a first layer comprising a plurality of reservoirs and a substantially planar second layer comprising a plurality of nonplanar elements elevated above the plate forming the tip electrodes, wherein the target-facing opening of the tip electrode is centered above each reservoir in the first layer, and wherein the lumen of the tip electrode communicates with the reservoir.

86. The system of claim 68, wherein the lumen of the at least one tip electrode comprises an electrically conductive medium.

87. The system of claim 68, wherein the housing of the at least one tip electrode comprises a tapered end.

88. The system of claim 68, wherein the electrically conducting surface of the at least one tip electrode comprises a coating at least partially coating walls of the housing defining the lumen.

89. The system of claim 68, wherein the electrically conducting surface comprises an element comprising an electrically conducting surface inserted into the lumen of the housing.

90. The system of claim 68, wherein the element is a cylinder, rod or wire.

91. The system of claim 68, wherein the electrically conducting surface is a structure penetrating the walls of the housing on one or both sides of the housing.

92. The system of claim 68, wherein the electrically conducting surface is a wire connected on the outside of the housing to a ring plate.

93. The system of claim 68, wherein the electrically conductive medium is a liquid.

94. The system of claim 68, wherein the electrically conductive medium is a gel.

95. The system of claim 68, wherein the electrically conductive medium comprises an agent for delivery to a target.

96. The system of claim 68, wherein the housing comprises a material selected from the group consisting of glass, fused silica, plastic, ceramic, an elastomeric material, a polymer, metal, a non-conducting material coated at least partially with a conducting material, and a conducting material coated at least partially with a non-conducting material.

97. The system of claim 68, wherein the housing of the at least one tip-electrode further comprises a receiving end distal to the target-facing end and comprises an opening for receiving the electrically conductive medium.

98. The system of claim 68, wherein the at least one tip-electrode and/or electrode plate further comprises a conducting surface that functions as a counter electrode.

99. The system of claim 68, wherein the housing of the at least one tip electrode comprises a uniform inner diameter and uniform or varying outer diameter.

100. The system of claim 68, wherein the housing of the at least one tip electrode comprises a uniform outer diameter and uniform or varying inner diameter.

101. The system of claim 68, wherein the length of the at least one tip electrode is less than about 10 cm.

102. The system of claim 68, wherein the length of the at least one tip electrode is less than about 500 mm.

103. The system of claim 68, wherein the length of the at least one tip electrode is less than about 50 mm.

104. The system of claim 68, wherein the length of the at least one tip electrode is less than about 1 mm.

105. The system of claim 68, wherein the diameter of the opening at the target-facing end of the at least one tip electrode is less than or equal to about 5000 mm.

106. The system of claim 68, wherein the diameter of the opening at the target-facing end of the at least one tip electrode is less than about 100 mm.

107. The system of claim 68, wherein the diameter of the opening at the target-facing end of the at least one tip electrode is less than about 50 mm.

108. The system of claim 68, wherein the diameter of the opening at the target-facing end of the at least one tip electrode is less than about 10 mm.

109. The system of claim 68, wherein the diameter of the opening at the target-facing end of the at least one tip electrode is less is less than about 1 mm.

110. The system of claim 68, wherein the diameter of the opening at the target-facing end of the at least one tip electrode is less is less than about 100 nm.

111. The system of claim 68, wherein the diameter of the opening at the target-facing end of the at least one tip electrode is less than about 50 nm.

112. The system of claim 68, the electrode plate comprises at least one mounting point for receiving a tip electrode, and wherein the at least one mounting point comprises a flexible attachment point for receiving the tip electrode permitting vertical movement of a tip-electrode from the mounting point.

113. The system of claim 112, wherein the electrode plate comprises a plurality of mounting points.

114. The system of claim 112, wherein the plate comprises a row of mounting points for forming a linear array of tip-electrodes.

115. The system of claim 112, wherein the plate comprises a plurality of rows of mounting points for forming a two-dimensional array of tip-electrodes.

116. The system of claim 112, wherein the center-to-center distance of each mounting point corresponds to the center-to-center distance of wells in a microtiter plate.

117. The system of claim 112, wherein the electrode plate comprises at least one interface point for a voltage or current generator.

118. The system of claim 112, wherein the electrode plate comprises at least one interface point for interfacing with a fluid delivery device.

119. The system of claim 112, wherein the electrode plate comprises at least two layers including a conducting layer and an insulating layer.

120. The system of claim 112 or 119, wherein the electrode plate comprises a layer which functions as a counter electrode.

121. The system of claim 112, wherein the at least one mounting point comprises an aperture for receiving the tip-electrode.

122. The system of claim 69, wherein the electrode plate and/or container comprises at least one microfluidic channel.

123. The system of claim 68, further comprising a processor for controlling one or more parameters selected from the group consisting of: delivery of fluid to the at least one tip electrode, delivery of at least one agent to at least one tip electrode, filling of the tip electrode with an electrically conductive medium, voltage or current pulse parameters, scanning of the electrode plate comprising the at least one tip electrode relative to a target, scanning of a target relative to a tip electrode, vertical movement of a tip electrode, electrophoresis through a tip electrode, electroosmosis through a tip electrode, pumping of fluid through a tip electrode, and function of a system detector.

124. The system of claim 123, wherein the voltage or current pulse parameters are selected from the group consisting of pulse duration, waveform, and pulse amplitude.

125. The system of claim 123 or 124, wherein the system further comprises a user device comprising a graphical interface for displaying operations of the system and/or for altering system parameters.

126. The system according to claim 82, wherein the system further comprises a read-out device for displaying output from the detector.

127. The tip electrode of claim 1, wherein the tip electrode comprises a flexible portion.

128. The system of claim 68, wherein the at least one tip electrode comprises a flexible portion.

129. The system of claim 68, wherein the system further comprises a positioning mechanism for restricting vertical movement of the at least one tip electrode.

130. The system of claim 129, wherein the positioning mechanism is mounted to the target-facing end of the at least one tip electrode.

131. The system of claim 129, wherein the positioning mechanism is an integral part of the tip electrode.

132. The tip electrode of claim 2, wherein the tip comprises holes in the portion of the tip proximal to the target facing end.

133. The electrode plate of claim 39, wherein at least one tip comprises holes in a portion of the tip proximal to its target facing end.

134. The tip electrode of claim 1, wherein the electrically conductive surface is a removable element from the housing.

135. The tip electrode of claim 1, wherein the electrically conductive surface is an integral component of the housing.

136. The tip electrode of claim 1, wherein the electrically conductive surface is coupled to a power supply through one or more connections at the receiving end.

137. The tip electrode of claim 42, wherein the electrically conducting surface comprises a structure conformed to fit into the housing defining the lumen of the tip electrode.

138. The tip-electrode plate of claim 42, wherein the electrically conductive surface is a removable element from the housing.

139. The tip-electrode plate of claim 42, wherein the electrically conductive surface is an integral component of the housing.

* * * * *

UNITED STATES PATENT AND TRADEMARK OFFICE
CERTIFICATE OF CORRECTION

| | | |
|---|---|---|
| PATENT NO. | : 7,456,012 B2 | Page 1 of 1 |
| APPLICATION NO. | : 10/726381 | |
| DATED | : November 25, 2008 | |
| INVENTOR(S) | : Frida Ryttsen et al. | |

It is certified that error appears in the above-identified patent and that said Letters Patent is hereby corrected as shown below:

On the Title page (30) in the section designeded "Foreign Application Priority Data" please add:

November 6, 1997     (SE)     9704076-0

Signed and Sealed this

Twenty-seventh Day of January, 2009

JOHN DOLL
*Acting Director of the United States Patent and Trademark Office*